United States Patent [19]
Montminy et al.

[11] Patent Number: 5,849,493
[45] Date of Patent: Dec. 15, 1998

[54] SCREENING ASSAY FOR COMPOUNDS STIMULATING SOMATOSTATIN TRANSCRIPTION FACTOR -1 BINDING TO AN STF-1 BINDING SITE

[75] Inventors: Marc Montminy, Wellsley, Mass.; Bernard Peers, Waremme, Belgium

[73] Assignee: Research Development Foundation, Carson City, Nev.

[21] Appl. No.: 757,316

[22] Filed: Nov. 27, 1996

Related U.S. Application Data

[60] Provisional application No. 60/007,722 Nov. 30, 1995.
[51] Int. Cl. [6] ............................... C12Q 1/02; C12Q 1/68
[52] U.S. Cl. ...................................... 435/6; 435/4
[58] Field of Search .............................. 435/6, 4

[56] References Cited

U.S. PATENT DOCUMENTS 5,612,455  3/1997  Hoey ........................................ 530/350

OTHER PUBLICATIONS

Olson et al., Proc. Natl. Acad. Sci. USA 92:9127–9131 (1995).

*Primary Examiner*—Johnny F. Railey, II
*Attorney, Agent, or Firm*—Benjamin Aaron Adler

[57]  ABSTRACT

The present invention provides a method to design compounds that mimic the effects of Pbx in stabilizing STF-1 binding. Using well known DNA binding assays, a person having ordinary skill in this art would be able to screen compounds to determine drugs effective in promoting STF-1 binding to DNA. In this way, one will be able to discover new compounds useful in stimulating somatostatin and insulin production.

6 Claims, 22 Drawing Sheets

```
P      GATCTAGAGCCCTTAATGGGCCAAA
       ATCTCGGGAATTACCCGGTTTCTAG

TSE₁   GATCTTGCGAGGCTAATGGTGCG
       AACGCTCCGATTACCACGCCATG

Flat   GATCTTGTTAATAATCTAATTACCGTAG
       AACAATTATTAGATTAATGGCATCATC
```

FIGURE 2E (cont.)

```
         119       123
WT  — F  P  W  M  K —
      ↓  ↓  ↓  ↓  ↓
Mut. — A  A  G  G  Q —
```

FIGURE 3C

| | Name | MOTIF | Distance N term from homeodomain (residues) |
|---|---|---|---|
| Rat | STF | FPWMK | 22 |
| Drosophila (ANT and BX Complex) | Labial (lab) | YKWMQ | 120 |
| | Proboscipedia (pb) | YPWMK | 28 |
| | Deformed (dfd) | YPWMK | 17 |
| | Sex Combs reduced (Scr) | YPWMK | 14 |
| | Antennapedia (Antp) | YPWMR | 8 |
| | Ultrabithorax (Ubx) | YPWMA | 50 |
| | Abdominal-A (AbdA) | YPWMT | 24 |
| Drosophila (orphan homeobox) | Caudal (cad) | FDWMK | 15 |
| C elegans (HOM complex) | mab5 | FPWMK | 8 |
| | lin39 | YPWMT | 11 |
| Human (Hox complex) | Hox B1 | FDWMK | 18 |
| | Hox B2 | FPWMK | 43 |
| | Hox B3 | FDWMK | 53 |
| | Hox B4 | YPWMR | 15 |
| | Hox B5 | FPWMR | 12 |
| | Hox B6 | YPWMQ | 13 |
| | Hox B7 | YPWMR | 5 |
| | Hox B8 | FPWMR | 6 |
| Mammalian (orphan homeobox) | Hox 11 | FPWMK | 23 |
| | m cdx$_1$ | YAWMR | 11 |
| | m cdx$_2$ | CEWMR | 15 |
| | m cdx$_4$ | YAWMR | |
| Sea urchin | Hox$_1$ | YPWMK | 11 |
| | CONSENSUS | $^Y_F$ PWM $^K_R$ | |

FIGURE 4

SCREENING ASSAY FOR COMPOUNDS STIMULATING SOMATOSTATIN TRANSCRIPTION FACTOR -1 BINDING TO AN STF-1 BINDING SITE

This non-provisional application claims benefit of Provisional Ser. No. 60/007,722 filed on Nov. 30, 1995.

BACKGROUND OF THE INVENTION

1. Field of the Invention

The present invention relates generally to the fields of biochemical endocrinology, molecular biology and protein chemistry. More specifically, the present invention relates to a screening assay for compounds stimulating somatostatin and insulin production.

2. Description of the Related Art

Glucose homeostasis requires the concerted efforts of numerous neuroendocrine systems. Pancreatic islets, however, are considered to be the primary "glucose sensor" in mammals. Islets contain four populations of cells which are characterized primansulin, glucagon, somatostatin or pancreatic polypeptide. Among these, insulin-producing β-cells predominate. Insulin secretion and production are stimulated by increases in serum glucose, an event which is mandatory for subsequent glucose uptake in certain tissues. Hence, dysfunction or destruction of β-cells results in elevated serum glucose levels, ultimately developing into diabetes.

Genetic linkage analysis indicates that hereditary factors strongly influence susceptibility to acquisition of the diabetic state. For example, at least 18 genetic loci have some degree of linkage to insulin-dependent diabetes mellitus (IDDM). One disease susceptibility locus, termed IDDM2, encompasses the human insulin gene and is associated with altered transcriptional regulation of insulin promoter function. Hence, disruption of the processes that regulate insulin gene expression may account in part for diabetogenesis. Consistent with this hypothesis, impaired β-cell function is a very common feature of diabetes.

Non-insulin dependent diabetes mellitus (NIDDM) is thought to occur as a result of both external and complex genetic influences. Interestingly, allelic variants at the insulin locus itself have been associated with the disease. These variants appear to contain a normal insulin gene, but exhibit altered properties with regard to transcriptional regulation.

Estimates indicate that as many as 20 million Americans may suffer from Type II diabetes. The progression of the disease appears to require both environmental factors and certain as yet largely unidentified diabetes susceptiblility genes, which may contribute to the peripheral insulin resistance of type II diabetes, in which tissues fail to utilize glucose appropriately in response to the insulin signal. Alternatively, genetic factors may account for the reduced glucose sensitivity of the insulin-producing pancreatic β-cells in these individuals. The end result of both of these physiological states is the marked hyperglycemia which constitutes the primary hallmark of diabetes.

Transcriptional control of the insulin gene is achieved through a short region of flanking DNA that interacts with cell-specific and glucose-sensitive signalling molecules. The precise nature of this regulatory organization remains poorly understood, although it is generally acknowledged that basic helix-loop-helix (bHLH) and homeodomain-containing factors are critical components of the transcriptional machinery that governs β-cell-specific expression of insulin. An islet-specific basic helix-loop-helix complex interacts with a proximal E-box that has been variously termed Nir, IEB1 or ICE; this element is present rat insulin I gene, but only once in the rat insulin II and human insulin genes.

Transient assays in insulin-producing cell lines suggest that E-box-binding factors synergize with β-cell-specific proteins that bind a nearby AT-rich sequence termed FLAT, which bears the hallmarks of a homeodomain recognition sequence. FLAT binding factors include Isl-1, lmx-1, cdx-3 and STF-1. In addition, the latter of these corresponds to the principal binding activity at an evolutionarily conserved AT-rich sequence termed the P-element. Isl-1 binds the FLAT element weakly and does not appear to be present in the FLAT-binding complexes detected with extracts from insulin-producing cells. Current evidence supports a more important role for Isl-1 in neural development. The homeodomain factors lmx-1 and cdx-3 have interesting transactivation properties with regard to insulin promoter function in heterologous cells, but their cellular distribution and FLAT-binding ability inside the β-cell remains unclear. In addition, there is little data that address directly the function of these factors in β-cell lines.

Within the group of factors with insulin promoter-binding activity, STF-1 is perhaps the most promising candidate for a bona fide regulator of insulin promoter function. In mice, STF-1 is first detected at embryonic day 8.5 in the nuclei of primordial cells that gives rise to the pancreas, shortly prior to the earliest detected expression of insulin in this region. Throughout the ensuing development of the endocrine pancreas, STF-1 and insulin are largely coexpressed. In addition, in extracts from insulin-producing cells lines, STF-1 appears to be a component of the endogenous DNA-binding activity at both the FLAT and P elements in the insulin promoter. STF-1 also synergizes strongly with the E-box-binding factor Pan-1, as might be expected from a FLAT-binding factor. However, DNA-binding assays indicate that other, unknown, factors from β-cell extracts also make a large contribution to the detected FLAT-binding activity. It remains unclear whether FLAT-mediated insulin promoting activity requires all, or only a subset, of these detected species.

The adult pancreas consists of both endocrine and exocrine components which are thought to arise from common precursor cells in the developing gut. Such precursor cells express the homeodomain protein refered to as STF-1 (14, 20) (or IPF-1 (19), IDX (17) or X1Hbox 8 (22)), the importance of which is illustrated by "knockout" studies where targeted disruption of the STF-1 gene leads to congenital absence of the pancreas (10). Although STF-1 is initially expressed in both exocrine and endocrine cells of the developing pancreas, the production of STF-1 is progressively restricted to insulin and somatostatin producing islet cells (7). In these cells, STF-1 action appears to be important for maintaining high level expression of both somatostatin and insulin genes (14, 17, 19, 20, 22).

STF-1 recognizes two well defined islet-specific elements on the insulin promoter, termed FLAT and P. When bound to these sites, STF-1 stimulates insulin transcription in concert with E47, a helix-loop-helix protein which recognizes two E-box elements termed Far and Nir. Similarly, STF-1 regulates somatostatin expression in islet cells via two islet specific elements, termed TSEI and TSEII (14, 17).

In addition to transcription stimulation of certain genes, homeodomain proteins such as STF-1 have been found to play an important role in development by establishing cell or segmental identity. In contrast to their specific and distinct effects in vivo, most homeodomain proteins exhibit low and overlapping DNA binding specificity in vitro. However, recent studies have implicated certain protein co-factors as determinants of homeodomain DNA binding specificity in vivo (8, 13). In Drosophila, for example, extradenticle (exd) has been shown to modulate the activity of homeotic proteins without altering their pattern of expression (21, 24). Rather, extradenticle appears to promote target gene selection by enhancing the DNA binding specificity of certain homeodomain proteins (2, 25). Indeed, extradenticle is highly conserved in vertebrates, sharing extensive sequence similarity (71%) with the human proto-oncogene Pbx1 (23).

The prior art is deficient in the lack of effective means of enhancing the binding of homeodomain proteins such as STF-1. The present invention fulfills this longstanding need and desire in the art.

SUMMARY OF THE INVENTION

A number of homeodomain proteins have been shown to regulate cellular development by stimulating the transcription of specific target genes. In contrast to their distinct activities in vivo, however, most homeodomain proteins bind indiscriminately to potential target sites in vitro, suggesting the involvement of cofactors which specify target site selection. One such co-factor, termed extradenticle (exd) has been shown to influence segmental morphogenesis in Drosophila by binding cooperatively with certain homeodomain proteins to target regulatory elements. The present invention demonstrates that STF-1, an orphan homeodomain protein required for pancreatic development in mammals, stimulates transcription of the pancreatic islet hormone gene somatostatin by binding cooperatively to DNA with Pbx, the mammalian homologue of extradenticle. Cooperative binding with Pbx requires a pentapeptide motif (FPWMK) which is well conserved among a large subset of homeodomain proteins. The FPMWK motif is not sufficient to confer Pbx-cooperativity to other homeodomain proteins, however, the N-terminal arm of the STF-1 homeodomain is also essential. As cooperative binding with Pbx occurs on only a subset of potential STF-1 target sites, the present invention shows that Pbx may specify target gene selection in the developing pancreas by forming heterodimeric complexes with STF-1. Indeed, the present invention demonstrates that the TSEII element of the somatostatin promoter recognizes a heteromeric complex composed of STF-1 and Pbx in pancreatic islet cells. Thus, specificity of STF-1 action in the pancreas may in part be dictated by the ability of potential target promoter sites to recognize the STF-1 Pbx heteromeric complex.

Thus, in one embodiment of the present invention, there is provided a DNA binding assay to determine compounds effective for promoting STF-1 binding to an STF-1 binding site, comprising the steps of: combining end-labeled, double-stranded DNA having an STF-1 binding site with STF-1 as a control in a first container; combining end-labeled, double-stranded DNA having an STF-1 binding site with STF-1 and a test compound as a sample in a second container; incubating said first and second containers; loading said control and said sample onto an electrophoresis gel; applying an electrical current to said electrophoresis gel so as to cause said control and said sample to migrate within said gel; detecting said control and said sample; comparing migration of said control to migration of said sample, wherein if said sample has a slower migration than said control, said test compound is effective in promoting STF-1 binding to said STF-1 binding site.

In another embodiment of the present invention, there is provided a DNA binding assay to determine compounds effective for promoting STF-1 binding to an STF-1 binding site, comprising the steps of: transfecting a first expression plasmid that consistuitively expresses STF-1 and a second expression plasmid that expresses a reporter gene under the control of an STF-1 binding site into an appropriate cell line; transfecting a third plasmid into said transfected appropriate cell line, said third expression plasmid expressing a trest compound; measuring an amount of transcription of said reporter gene, wherein if said transcription takes place, said test compound is effective for promoting STF-1 binding to said STF-1 binding site.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention can be understood in detail, more particular descriptions of the invention briefly summarized above may be had by reference to certain embodiments which are illustrated in the appended drawings. These drawings form a part of the specification. It is to be noted, however, that the appended drawings illustrate preferred embodiments of the invention and therefore are not to be considered limiting in their scope.

FIG. 1A shows a gel mobility shift assay of crude nuclear extracts from pancreatic islet Tu-6 cells using a double stranded somatostatin TSEII oligonucleotide extending from −303 to −281. C1, C2, and C3, protein DNA complexes as indicated. Crescendo bar indicates increasing amount of nuclear extract. STF, recombinant STF-1 protein only; Tu-6 NE and Hela NE, nuclear extract from Tu-6 and Hela cells, respectively. PI, pre-immune antiserum. STF-1 Ab, STF-1 antiserum raised against the C-terminal part of STF-1 protein. STF-1 Ab+ Oct oligo, STF-1 antiserum plus Oct 1 binding site (Sph1 motif) of SV40. Oct. Ab, monoclonal Oct 1 antiserum (gift of W. Herr) raised against human Oct. 1 protein. FIG. 1B shows an off-rate analysis of complexes formed with somatostatin TSEII probe and Tu6 nuclear extract (preincubated with unlabeled Oct1 oligo to analyze only C1 and C2 complex) as described below. Complexes C1 and C2 as indicated. Time (in minutes) after addition of 1000-fold excess of unlabeled TSEII competitor DNA indicated over each lane. PI, pre-immune serum; STF-1 Ab, STF-1 antiserum added to gel shift assay. FIG. 1C shows a gel mobility shift analysis of recombinant STF-1 protein, using the somatostatin TSEII oligo as probe. STF-1 binding activity was tested in the absence (−) or presence (+) of heterologous nuclear extract from Jurkat cells, which do not contain detectable levels of STF-1 protein by Western blot assay. Crescendo bars indicate increasing amount of recombinant STF-1 protein. Complexes C1 and C2 as indicated. FIG. 1D shows an off-rate of complexes C1 and C2 in reconstituted extracts containing recombinant STF-1 plus Jurkat nuclear extract. Time points (in minutes) after addition of unlabeled TSE II competitor (1000-fold excess) as indicated over each lane.

FIG. 2A shows a gel mobility shift assay of Tu6 NE using TSE II oligonucleotide as probe. Complexes C1, C2, and C3 as indicated. PBX Ab, Pbx antiserum included in reaction. PI, pre-immune serum. STF-1 Ab, STF-1 antiserum. FIG. 2B shows the effect of in-vitro translated Pbx protein (PBX) on STF-1 binding activity. Gel mobility shift assay using TSE II oligonucleotide plus STF-1 and/or Pbx as indicated over each lane. TNT, control lysate. FIG. 2C shows that PBX stabilizes STF-1 binding to TSEII complex. Off-rate analysis of STF-1 and STF-1 Pbx complexes using somatostatin TSE II oligonucleotide as probe. Time (in minutes) after addition of excess unlabeled TSE II oligo as indicated. Complexes C1 and C2, corresponding to STF-1 monomer and STF-1/PBX heterodimer, respectively, as indicated. FIG. 2D shows an analysis of STF-1/Pbx heterodimer formation on somatostatin and insulin promoter sequences. TSEII, wild-type TSE II oligonucleotide. M1, M2, and M3; mutant TSEII oligonucleotides in which TAAT motifs were mutated as shown in FIGS. 3D and 3E. P and FLAT, insulin I promoter elements which recognize STF-1 with high affinity. TSEI, somatostatin promoter element which binds STF-1. PBX, in vitro translated PBX protein added to binding reactions; STF, full length recombinant STF-1 protein. FIG. 2E shows the sequence of wild-type and mutant oligonucleotides used in gel shift assays in FIG. 3B. Brackets indicate consensus TAAT motifs which were targeted for mutagenesis. FIG. 2F shows that STF-1 and Pbx act cooperatively on a subset of promoter sites. Transient transfection assay of GC cells using STF-1 and E2A-Pbx effector plasmids as indicated below each bar. Bar graph shows luciferase activity derived from reporter construct containing minimal growth hormone (GH) promoter alone (Luc), with two copies of the somatostatin TSEII element upstream of the GH promoter (TSEII-Luc), or two copies of the insulin P element (P-Luc). Activities were normalized to co-transfected RSV-CAT control plasmid.

FIG. 3A–E shows the conserved pentapeptide motif in STF-1 is critical for cooperative binding with Pbx. FIG. 3A shows an analysis of STF-1 monomer (complex C1) and STF-1/Pbx heterodimer (complex C2) formation for wild-type and truncated recombinant STF-1 polypeptides. Deletion endpoints in mutant STF-1 polypeptides are indicated over each lane. For example, Δ1-70 indicates STF-1 polypeptide lacking residues 1–70. Hox 140–215, STF-1 homeodomain polypeptide. FIG. 3B shows a schematic representation of constructs used in gel shift assays above. H.D., STF-1 homeodomain (amino acid residues 140–215). Full length STF-1 protein extends from amino acid residues 1–284. FIG. 3C shows that mutagenesis of the conserved pentapeptide motif destroys cooperativity with Pbx sequence of wild-type and mutant STF-1 protein with amino acid numbers indicated. FIG. 3D shows a gel shift analysis of wild type (WT) and mutant (MUT) STF proteins alone and in combination with in vitro translated PBX or E. Jurkat nuclear extract.

FIG. 4 shows a pentapeptide motif in STF-1 which is necessary for heterodimer formation with Pbx on the somatostatin TSEII site is conserved in a number of homeobox proteins. Different homeobox proteins classified according to species and listed by name. For each protein, sequences related to motif in STF-1 listed in single amino acid code with distance N-terminal to the homeodomain indicated on right.

FIG. 5A shows a schematic of recombinant GST-fusion proteins used in gel shift assays below. Isl1 H.D., homeodomain of the lim domain factor Isl1. PBX interaction motif-Isl1 H.D., STF-1-Isl1 fusion protein containing STF-1 PBX interaction motif region (amino acid residues 110–138) fused to the Isl1 homeodomain. cdx3 H.D., homeodomain of the pancreatic homeobox protein cdx3 (amino acid residues 143–253). PBX interaction motif-cdx3, fusion protein containing STF-1 PBX interaction motif region (amino acid residues 110–138) fused to the cdx3 homeodomain (amino acid residues 176–253). PBX interaction motif-STF-1, STF-1 polypeptide containing the PBX interaction motif region (110–138) fused to the STF-1 homeodomain (amino acid residues 140–215). STF-1 H.D. STF-1 homeodomain alone without the PBX interaction motif region. FIG. 5B shows a gel mobility shift assay using the somatostatin TSEII site as $^{32}$P-labeled probe. – and + indicates absence or presence of reticulocyte lysate programmed with PBX RNA. Cooperativity with PBX tested with homeodomain fusion proteins shown over each lane. Monomeric and heterodimeric complexes as labeled.

FIG. 6A shows the structure and activity of STF-1/cdx3 fusion constructs. cdx3 sequences shaded, STF-1 sequences in white. Relative position of N-terminal arm (N), and Helices 1, 2, and 3 (H1, H2, H3) as indicated. Cooperative binding with Pbx in gel shift assays indicated (+, –) on right. FIG. 6B shows the amino acid alignment of STF-1 and cdx3 homeodomains shown below, with amino acid number of C-terminal residue shown on right. Dashes indicate amino acid identity between STF-1 and cdx3. Arrows point to amino acid endpoints (I, II, III) used for fusion constructs. FIG. 6C shows the gel shift assay of recombinant STF-1/cdx3 fusion proteins. Construct numbers refer to constructs depicted in schematic (top). Presence of in-vitro translated Pbx (PBX) or unprogrammed reticulocyte lysate (TNT) in binding reactions as indicated. C1, C2; complexes corresponding to STF-1 monomer and Pbx/STF-1 heterodimer, respectively.

DETAILED DESCRIPTION OF THE INVENTION

Figure 1A:
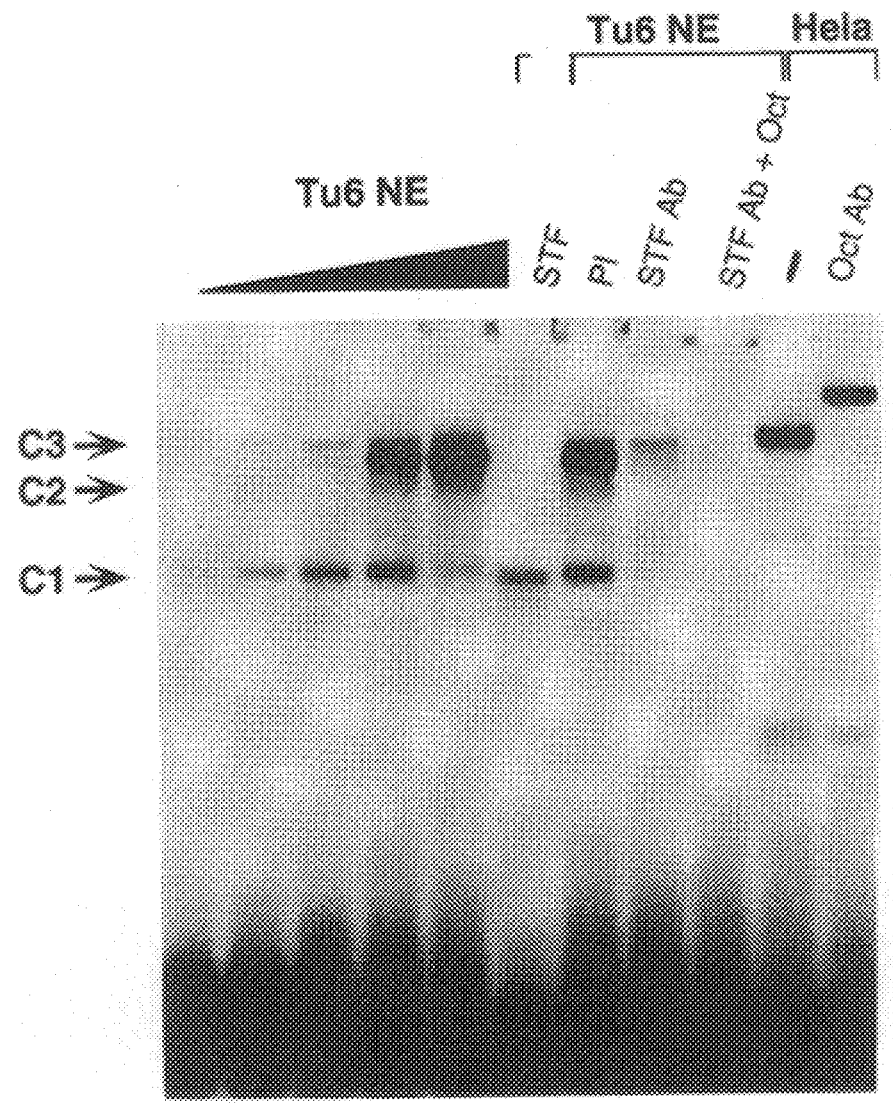
FIG. 1A–D shows the pancreatic homeobox factor STF-1 binds cooperatively to a cell specific regulatory element in the somatostatin promoter along with a ubiquitous nuclear factor.

The human genome contains four clusters of homeotic selector genes, termed Hox genes, which are critical determinants of axial body pattern formation during embryogenesis (Krumlauf, 1994 Cell 78:191–201). The four clusters each contain up to 13 genes, and a given gene in one cluster usually has particularly high homology with a member of the other three families. Such related genes are termed paralogs; hence HoxA1, HoxB1, HoxC1 and HoxD1 are all closely related paralogs, each in a different Hox cluster on a different chromosome. The HoxB complex is on the long arm of chromosome 17, and for example, HoxB1 through HoxB9 had been identified.

Glucose-dependent regulation of the insulin gene appears to occur in concert with glucose-mediated increases in the secretion of insulin. This may be due in part to increases in intracellular calcium. In addition, glucose-responsive insulin promoter function may occur at least in part by modulating the activity of FLAT-binding proteins. HoxB13 binds the functionally important FLAT element of the insulin promoter with high affinity. Additionally, HoxB13 and the insulin ICE/Nir element-binding factor Pan-1 strongly activate the insulin promoter when added in combination. This is consistent with the observation that the FLAT and Nir elements function synergistically in insulin-producing cells. Collectively, these data suggested that calcium-dependent signaling pathways might regulate the function of HoxB13.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

The amino acid described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomeclature, *J Biol. Chem.*, 243:3552–59 (1969), abbreviations for amino acid residues are shown in the following Table of Correspondence:

TABLE OF CORRESPONDENCE

| SYMBOL | | |
|---|---|---|
| 1-Letter | 3-Letter | AMINO ACID |
| Y | Tyr | tyrosine |
| G | Gly | glycine |
| F | Phe | Phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element (e.g., plasmid, chromosome, virus) that functions as an automous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in tis either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNApolymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the mdia, and this signal peptide is clipped off by the host cell before the protein leaves the cell. Signal sequences can be found associated with a variety of proteins native to prokaryotes and eukaryotes.

The term "oligonucleotide", as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use the method. For example, for diagnostic applications, depending on the complexity of the target sequence, the oligonucleotide primer typically contains 15–25 or more nueleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence or hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or monnon ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

The labels most commonly employed for these studies are radioactive elements, enzymes, chemicals which fluoresce when exposed to untraviolet light, and others. A number of fluorescent materials are known and can be utilized as labels. These include, for example, florescein, rhodamine, auramine, Texas Red, AMCA blue and Lucifer Yellow. A particular detecting material is anti-rabbit antibody prepared in goats and conjugated with fluorescein through an isothiocyanate.

Proteins can also be labeled with a radioactive element or with an enzyme. The radioactive label can be detected by any of the currently available counting procedures. The preferred isotope may be selected from $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

A particular assay system developed and utilized in the art is known as a receptor assay. In a receptor assay, the material to be assayed is appropriately labeled and then certain cellular test colonies are inoculated with a quantitiy of both the label after which binding studies are conducted to determine the extent to which the labeled material binds to the cell receptors. In this way, differences in affinity between materials can be ascertained.

An assay useful in the art is known as a "cis/trans" assay. Briefly, this assay employs two genetic constructs, one of which is typically a plasmid that continually expresses a particular receptor of interest when trnasfected into an appropriate cell line, and the second of which is a plasmid that expresses a reporter such as luciferase, under the control of a receptor/ligand complex. Thus, for example, if it is desired to evaluate a compound as a ligand for a particular receptor, one of the plasmids would be a construct that results in expression of the receptor in the chosen cell line, while the second plasmid would possess a promoter linked to the luciferase gene in which the response element to the particular receptor is inserted. If the compound under test is an agonist for the receptor, the ligand will complex with the receptor, and the resulting complex will bind the response element and initiate transcription of the luciferase gene. The resulting chemiluminescence is then measured photometrically, and dose response curves are obtained and compared to those of known ligands. The foregoing protocol is described in detail in U.S. Pat. No. 4,981,784 and PCT International Publication No. 88/03168.

The present invention discloses that STF-1 binds with Pbx and this binding leads to enhanced transcription of somatostatin and most likely insulin. The binding of STF-1 to Pbx requires a pentapeptide (FPWMK). STF-1 and Pbx act synergistically on only a subset of sites that recognize the STF-1-Pbx heterodimer. As shown below, amino acid residues 115–123 of STF-1 are required for cooperativity with Pbx. That is, since a mutant STF-1 cDNA could not cooperate with Pbx, the Pim is necessary. It is further shown that the flexible N-terminal art of STF-1 homoedomain including amino acid residues 145–153 are essential for cooperativity with Pbx.

The following examples are given for the purpose of illustrating various embodiments of the invention and are not meant to limit the present invention in any fashion.

EXAMPLE 1
Plasmid constructions and expression of proteins.

Figure 3A:
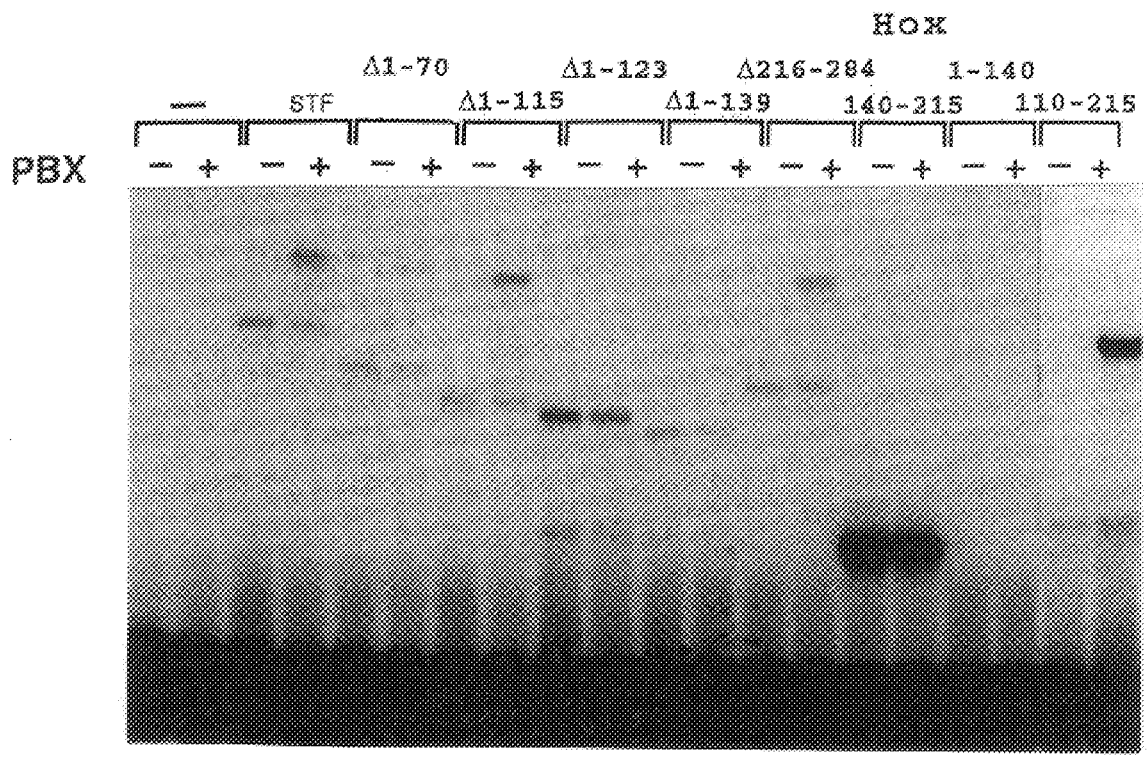
Figure 3B:
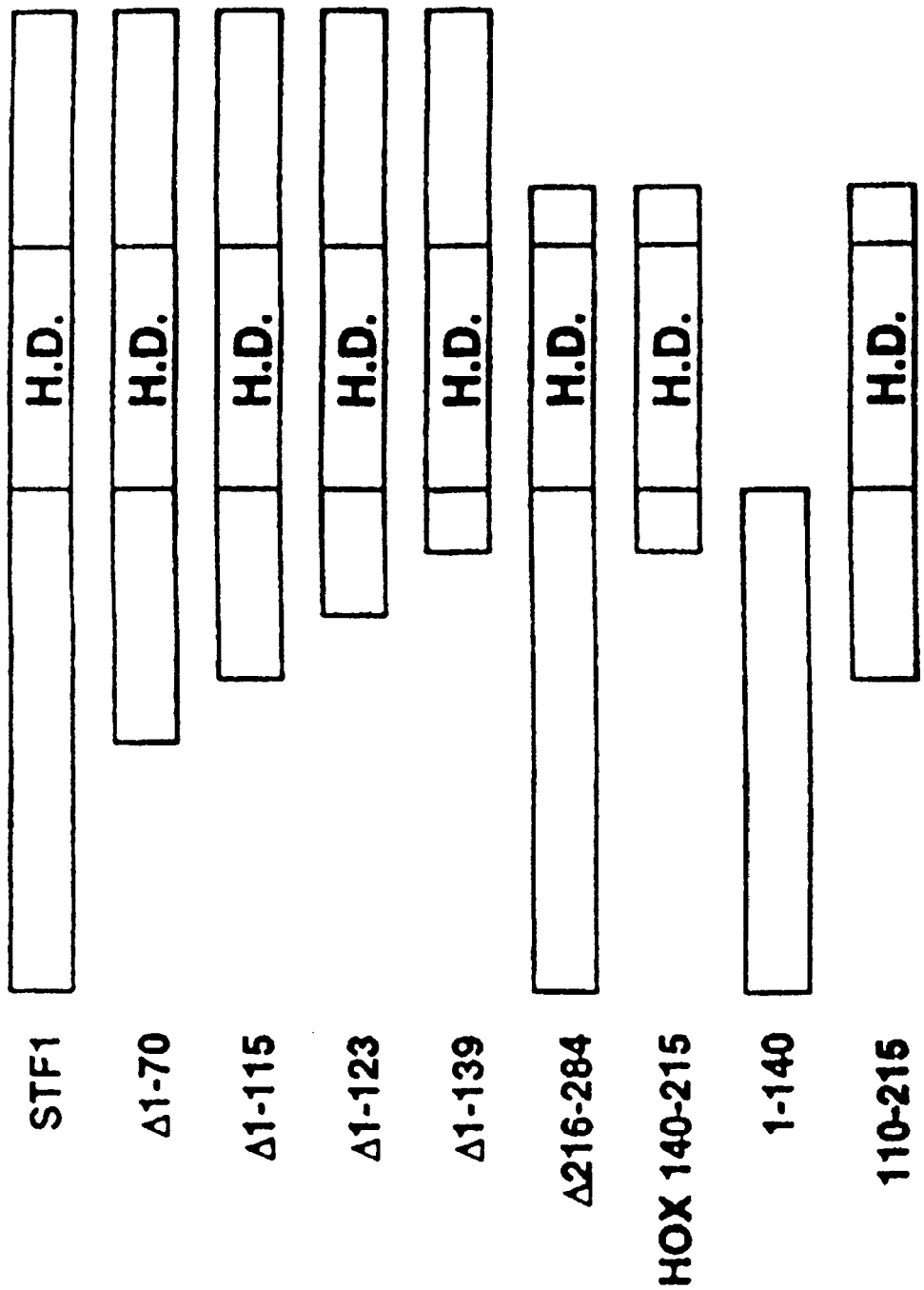

The STF-1 deletion constructs shown in FIG. 3B have been described previously (20). STF-1 deletion plasmids were constructed using a polymerase chain reaction (PCR) amplification procedure. Using the STF-1 cDNA as template, one sense oligonucleotide spanning the deletion was incubated with an anti-sense oligonucleotide corresponding to the 3' end of the STF-1 cDNA. STF-1 cDNA fragments containing appropriate deletions within the coding region were obtained by PCR amplification using Taq polymerase. The Pbx1 cDNA (gift of C. Murre) (18) and the STF-1 deletion mutants Δ1-70, Δ1-115, Δ1-139 and Δ216-284 were produced using the Promega TNT rabbit reticulocyte lysate couple transcription/translation system, according to the protocol of the manufacturer. The STF-1 full-length protein and the STF-1 deletion mutants hox 140-215, 1-140 and 110-215 (see FIG. 3A) were expressed in $E.\ coli$ using the bacterial expression vector pGEX3X. Recombinant proteins were purified as described previously (14); STF-1 polypeptides were initially expressed as fusion proteins which contained glutathione-S-transferase (GST) at their N-termini. The GST-STF-1 polypeptides were purified from bacterial lysates by affinity chromatography over glutathione sepharose resins. The purified proteins could then be eluted from the resins using glutathione (10 mM) or proteolytically cleaved by virtue of a factor X cleavage site which is inserted between the GST and STF-1 sequences. The recombinant proteins were eluted from the glutathione-sepharose beads by digestion with 4 $\mu$g of factor Xa for 16 hours at room temperature.

Figure 5A:
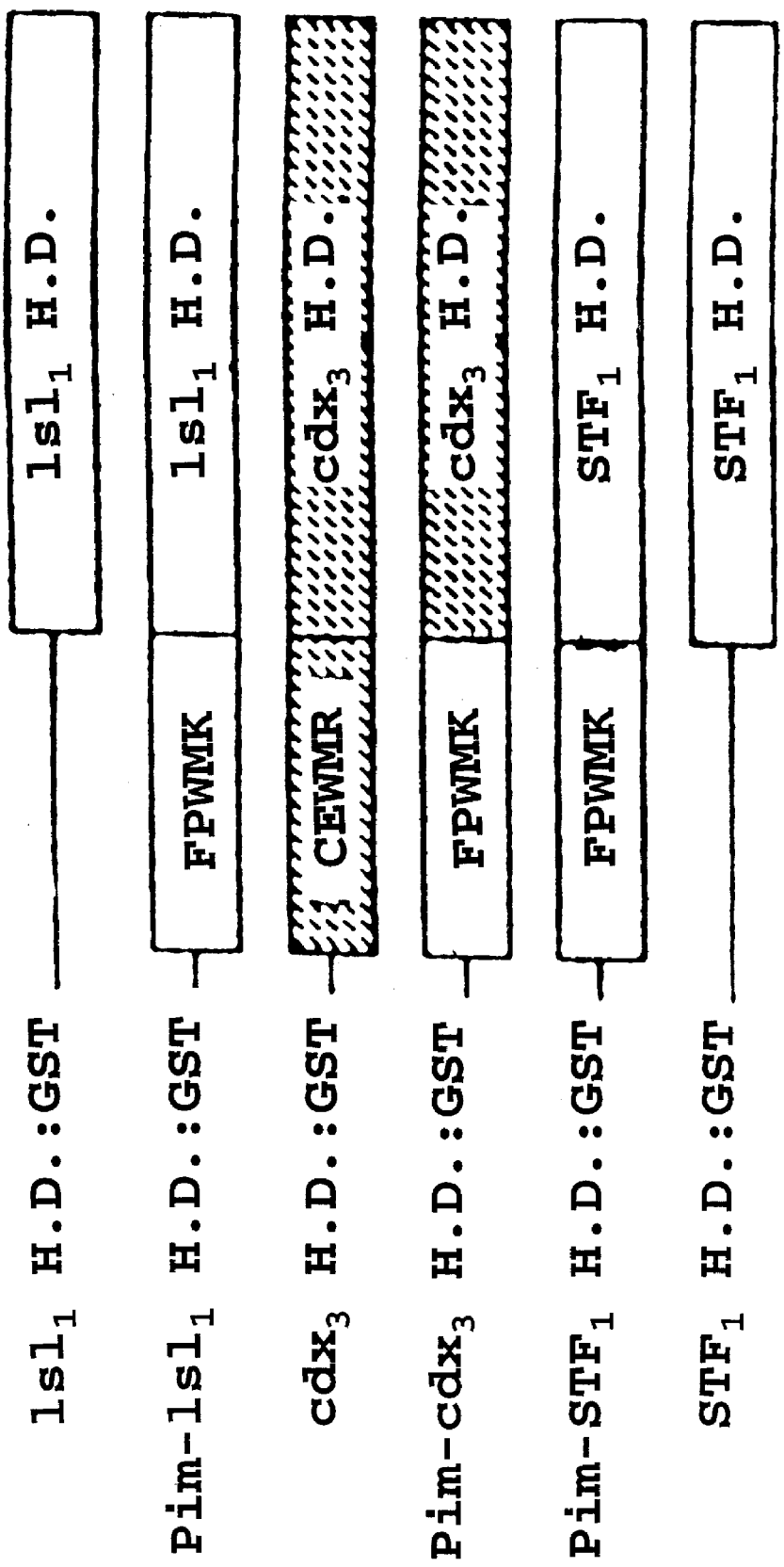
FIG. 5A–B shows the conserved PBX interaction motif (Pim) is necessary but not sufficient to promote cooperative binding between PBX and homeobox proteins.

The GST-fusion proteins described in FIG. 5 were also expressed in $E.\ coli$ using the pGEX3X vector. The sequences coding for the rat Isl1 homeodomain (12) (amino acid 176 to 248), for the hamster cdx3 homeodomain (6) (amino acid 143 to 253) and for the STF-1 homeodomain (amino acid 140 to 215) were amplified by polymerase chain reaction and fused in frame in the pGEX3X plasmid. For the PBX interaction motif-homeodomain fusion proteins, the STF-1 coding sequence from residue 110 to 138, encompassing the FPWMK motif, was ligated in frame upstream the coding sequence of the Isl1 homeodomain (amino acid 176 to 248), of the cdx3 homeodomain (amino acid 176 to 253) and of the STF-1 homeodomain (amino acid 140 to 215), and inserted in the pGEX3X vector. The GST-fusion proteins were expressed and purified as described previously (14) and eluted from the beads with 5 mM reduced gluthatione.

EXAMPLE 2
Gel mobility shift assays.

Figure 2A:
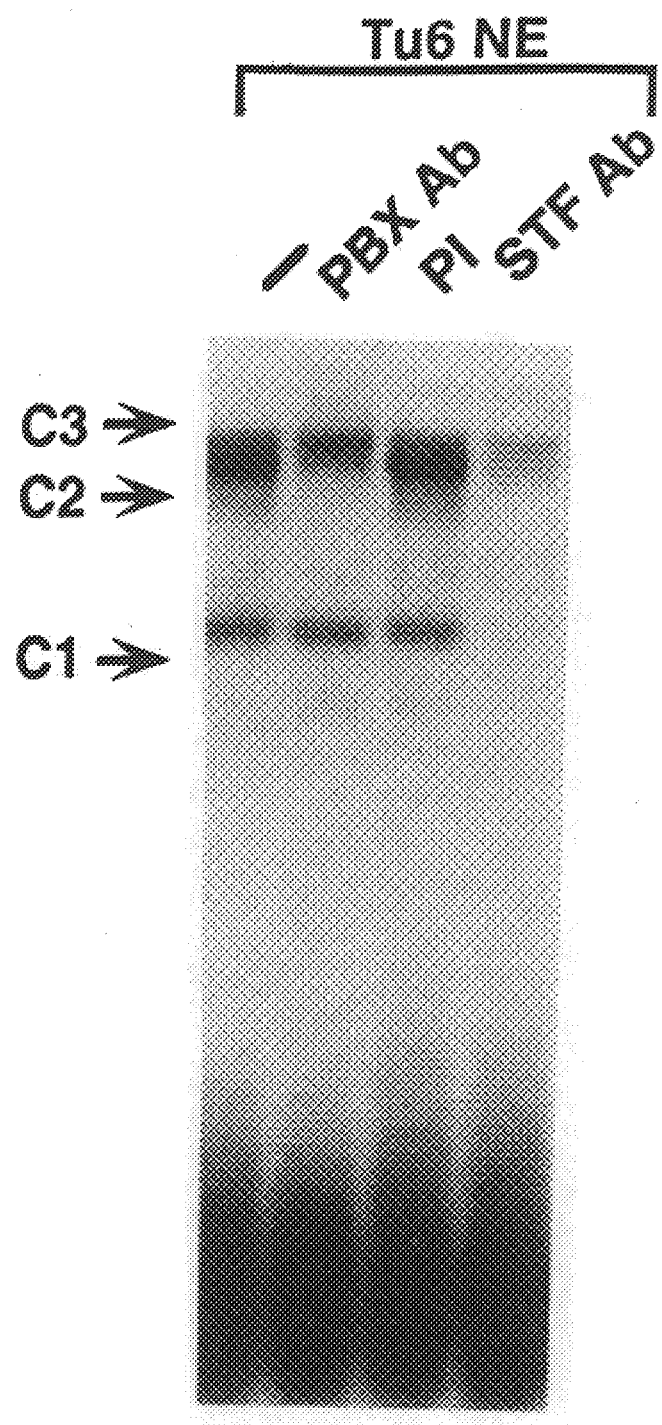
FIG. 2A–F shows that the ubiquitous homeobox protein Pbx forms a heterodimeric complex with STF-1 on the somatostatin TSEII element.
Figure 2B:
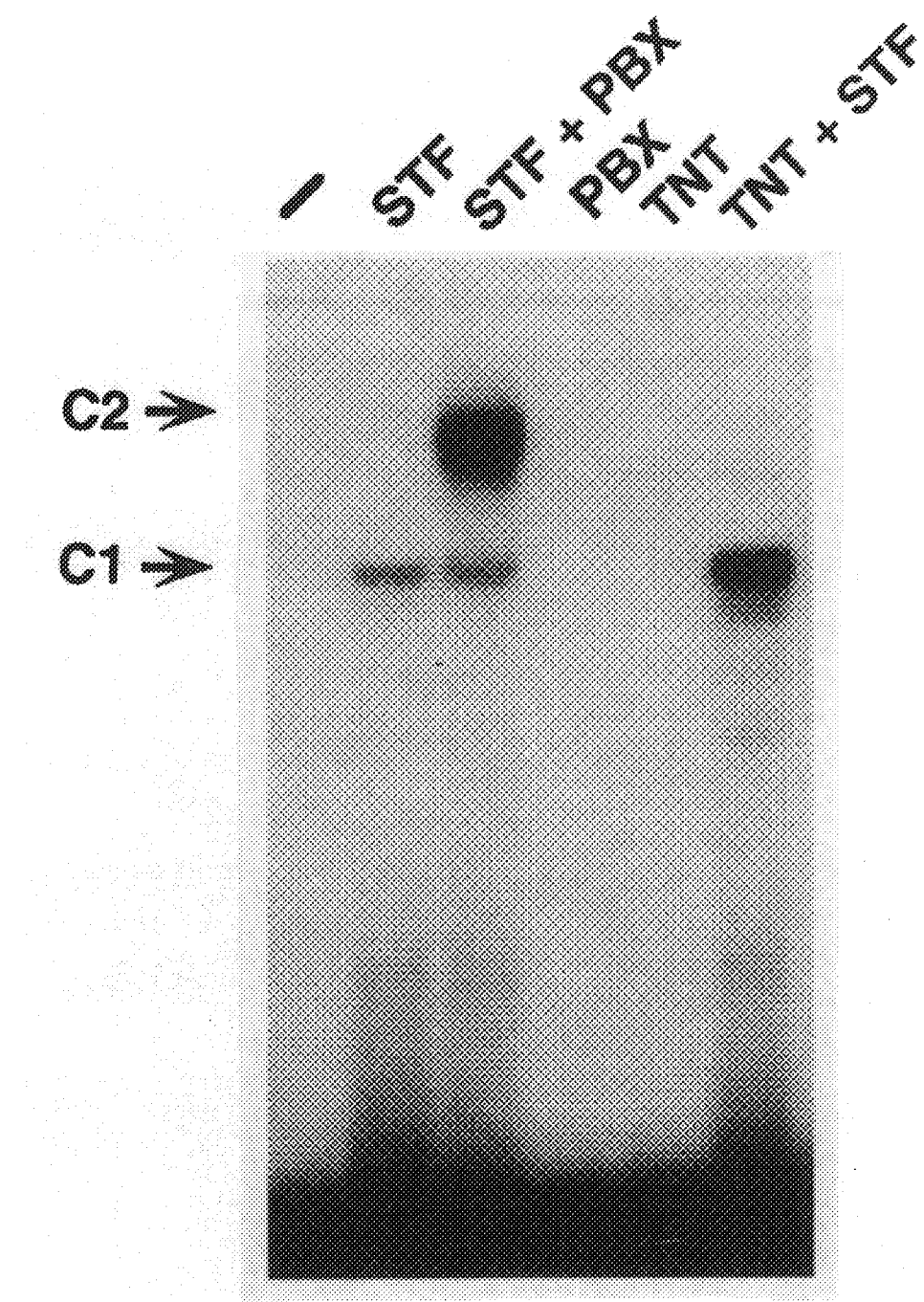
Figure 2C:
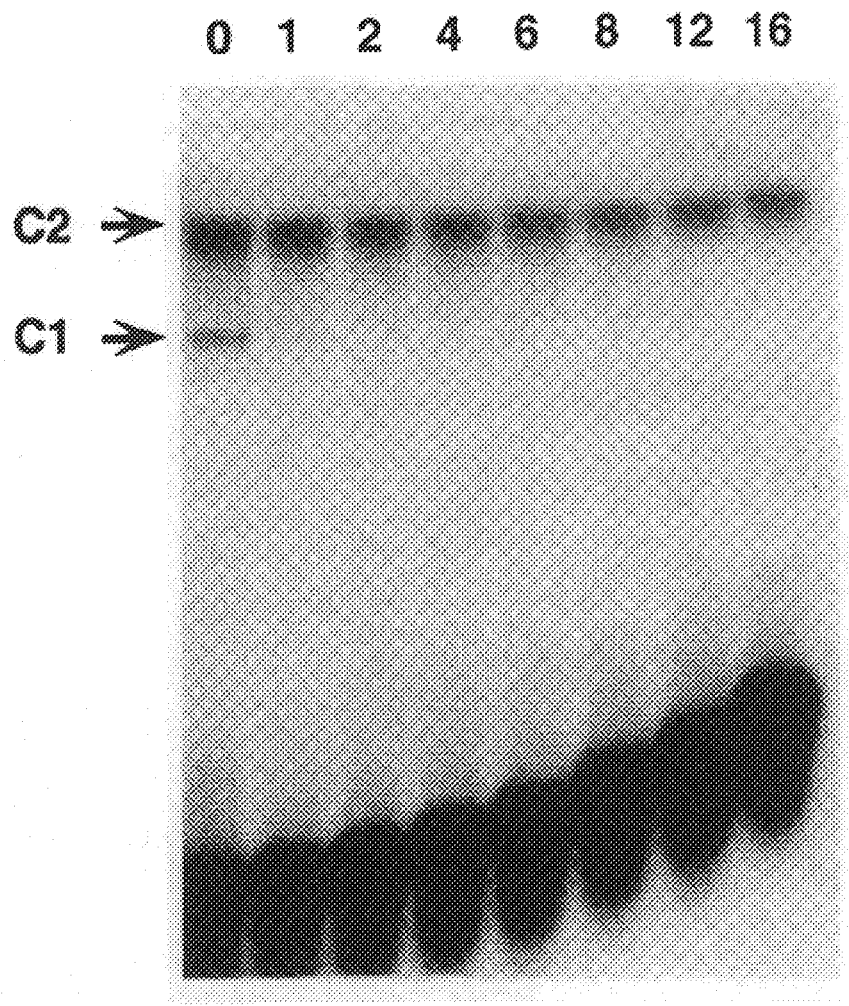

Gel mobility shift assays were performed exactly as described previously (20) using 0.1 ng of end-labeled double stranded oligonucleotide whose sequences are presented in FIG. 2C. For off-rate analysis, the TSEII probe was first incubated with the proteins at room temperature for 30 minutes, then a 1000-fold excess of unlabeled TSEII oligonucleotide was added and aliquots were loaded at various time points on a running gel. In supershift assays, TU6 nuclear cell extract was preincubated with 1 $\mu$l of Pbx (11) or STF-antiserum (20) for 15 minutes at room temperature before adding the TSEII probe. Pbx antiserum does not discriminate between members of the Pbx family (Pbx 1, 2, 3).

EXAMPLE 3
Specific Protein DNA Complexes C1, C2, And C3

In pancreatic tumor cell lines, expression of the pancreatic islet hormone genes somatostatin and insulin depends on the homeobox factor STF-1. STF-1 regulates somatostatin expression in Tu-6 cells by binding to two tissue specific regulatory elements termed TSEI and TSEII (14). Using a $^{32}$P-labeled TSEII site oligonucleotide probe in gel mobility shift assays of crude Tu-6 nuclear extract, three specific protein DNA complexes were detected and are referred to herein as complex C1, complex C2, and complex C3 (FIG. 1A). Complexes C1 and C2 were only observed in pancreatic islet cell extracts while complex C3 was detected at comparable levels in non islet lines such as Hela. Complex C3 appeared to contain the ubiquitous Oct-1 protein, as revealed by "supershift assay" with Oct-1 antiserum. By contrast, complexes C1 and C2 contained STF-1 protein, as determined by their sensitivity to addition of STF-1 antiserum.

Figure 1B:
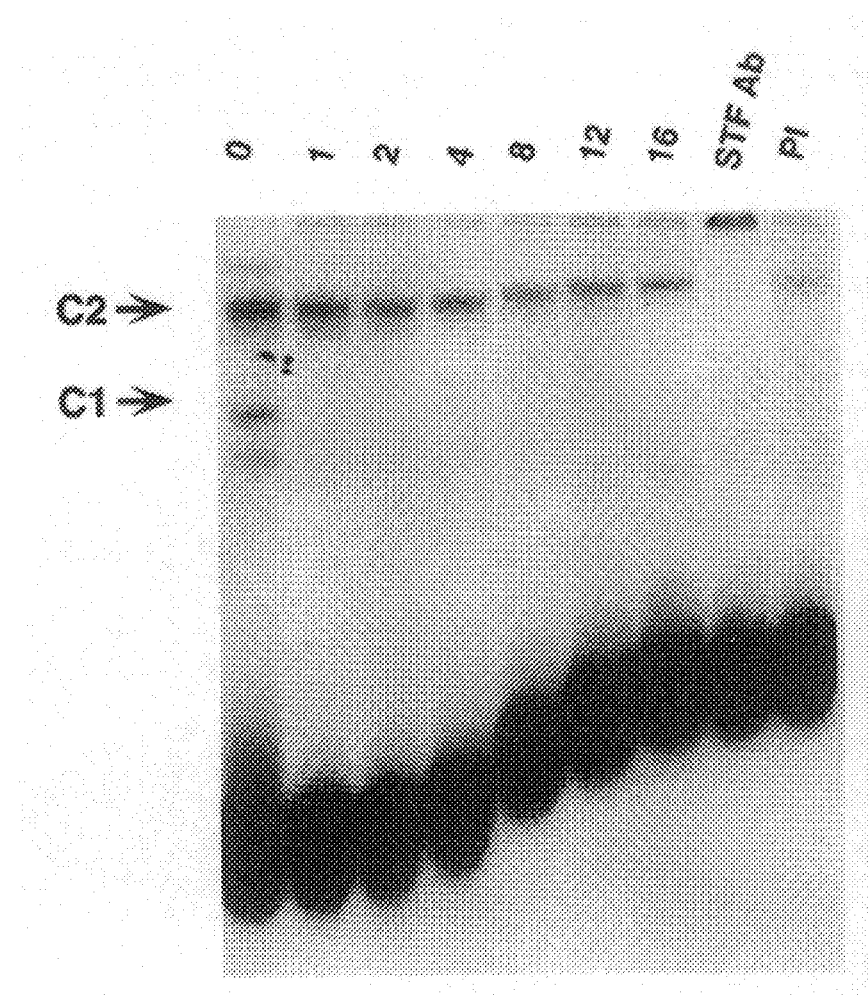

Complex C2 increased exponentially as a function of extract concentration whereas complex C1 increased linearly in gel mobility shift assays. Recombinant full length STF-1 protein generated a single complex migrating at the same position as complex C1 (FIG. 1A, lane 6), suggesting that complex C1 contains only STF-1 protein while complex C2 represents a high affinity heteromeric STF-1 complex. In this regard, off-rate studies indicated that the half life for complex C1 was less than 1 minute compared with a half life of about 15 minutes for the heteromeric STF-1 complex C2 (FIG. 1B).

Figure 1C:
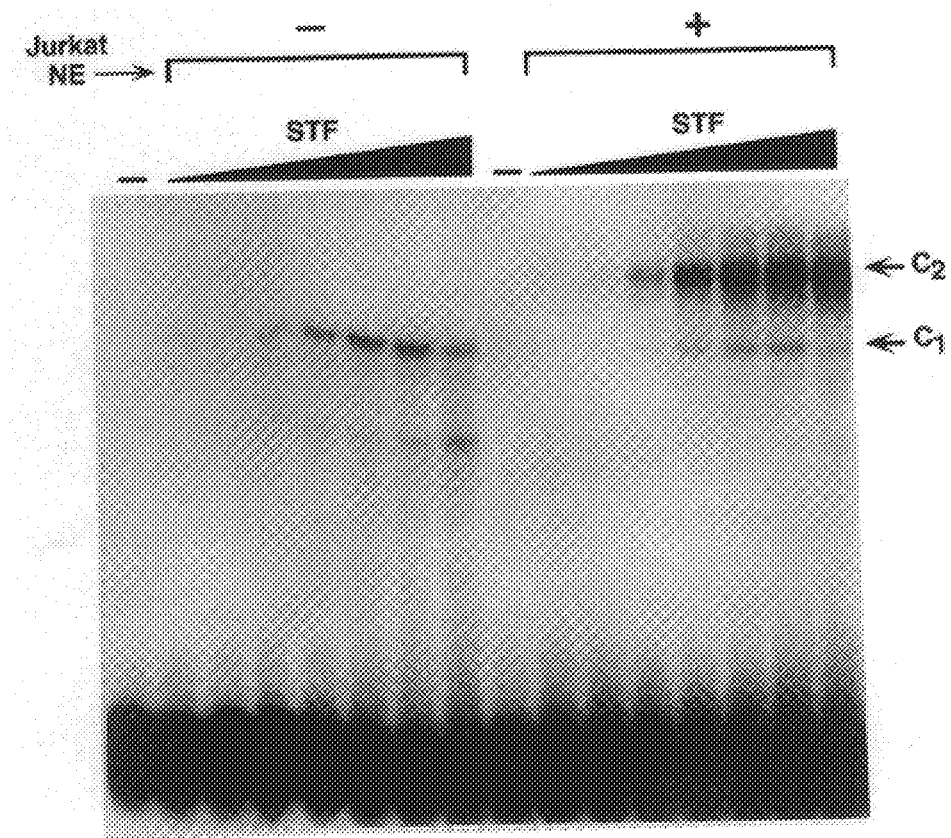

To confirm that the C2 complex does not correspond to a homodimeric form of STF-1, increasing concentrations of recombinant STF-1 protein were examined in gel mobility shift assays with the TSEII probe (FIG. 1C). No slower migrating complexes were observed with high amounts of STF-1 protein, indicating that complex C2 must contain an additional protein component which strongly stabilizes binding of STF-1 to DNA.

Figure 1D:
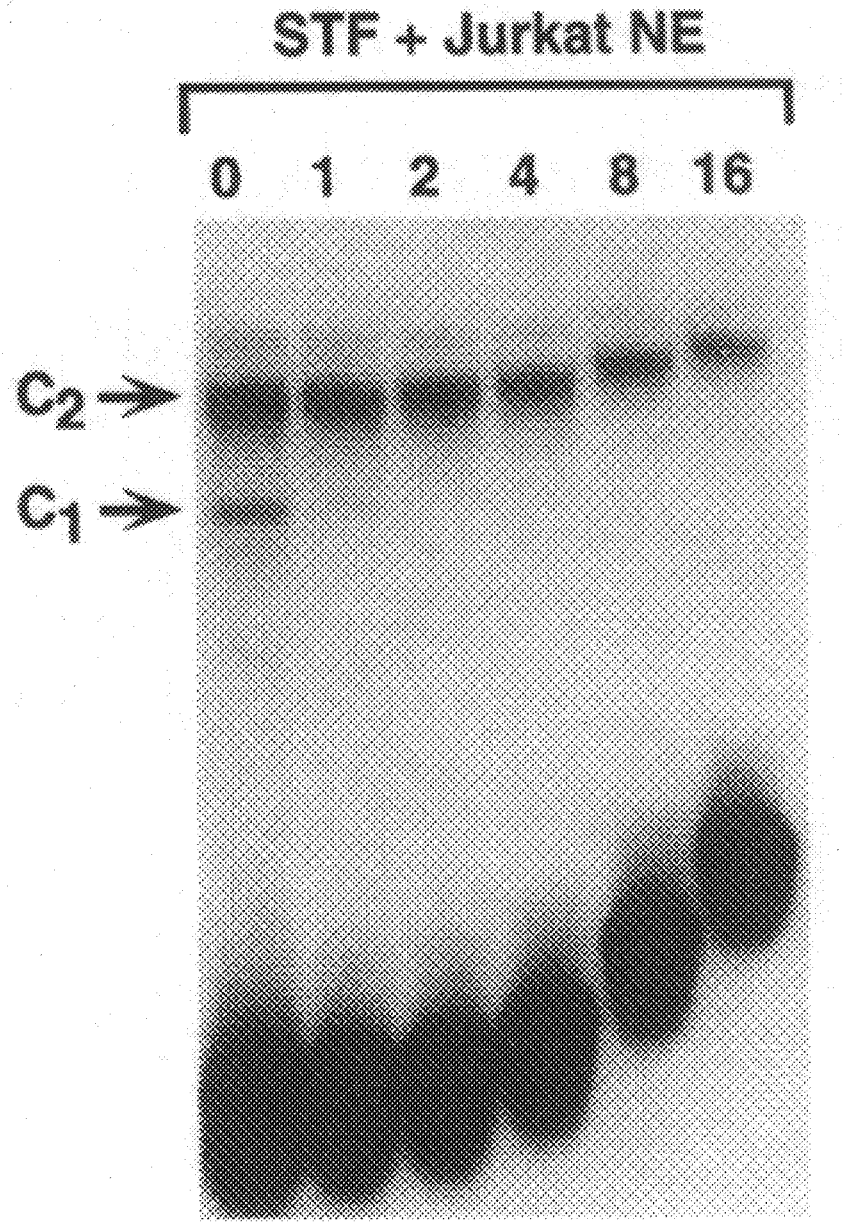

To demonstrate that this component was ubiquitously expressed, crude Jurkat (or Hela) nuclear extracts were added to reactions containing recombinant STF-1 protein. Under these conditions, formation of complex C2 was readily observed, and was dependent on addition of recombinant STF-1 (FIG. 1C). The off-rate for the C2 complex in reconstituted extracts was comparable to that in Tu-6 extracts (about 15 minutes), indicating that a ubiquitous factor stabilizes the binding of STF-1 to the TSEII site (FIG. 1D).

A Drosophila homeobox protein termed extradenticle binds cooperatively with other homeodomain proteins to target promoter sites (2, 25). Whether the mammalian homolog of extradenticle, termed Pbx (23), is contained in complex C2 was examined next. When added to crude Tu-6 nuclear extracts, Pbx antiserum specifically blocked formation of complex C2, but this antiserum had no effect on the formation of C1, which contains only STF-1 (FIG. 2A, lane 2). Moreover, co-incubation of Pbx and recombinant STF-1 proteins resulted in formation of the heteromeric C2 complex in gel shift assays (FIG. 2B). The stability of this Pbx-STF-1 complex, evaluated by off-rate analysis, was comparable to the endogenous C2 complex in Tu-6 nuclear extracts (FIG. 2C).

Figure 2D:
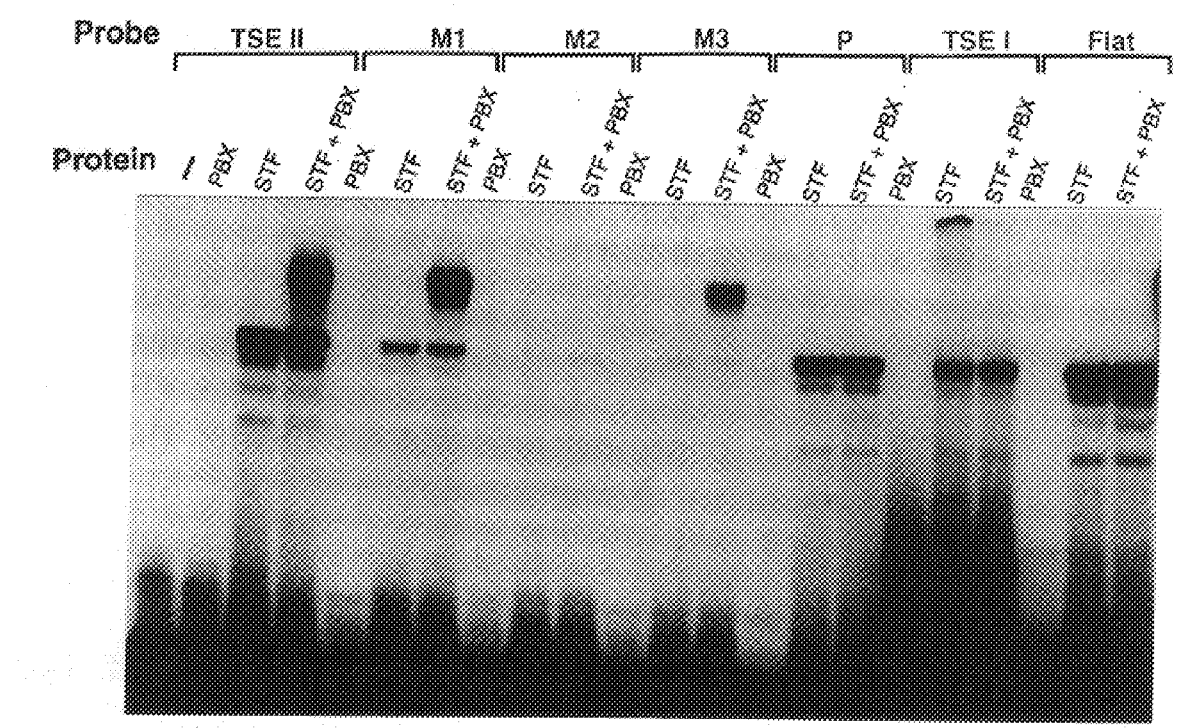
Figure 2E:
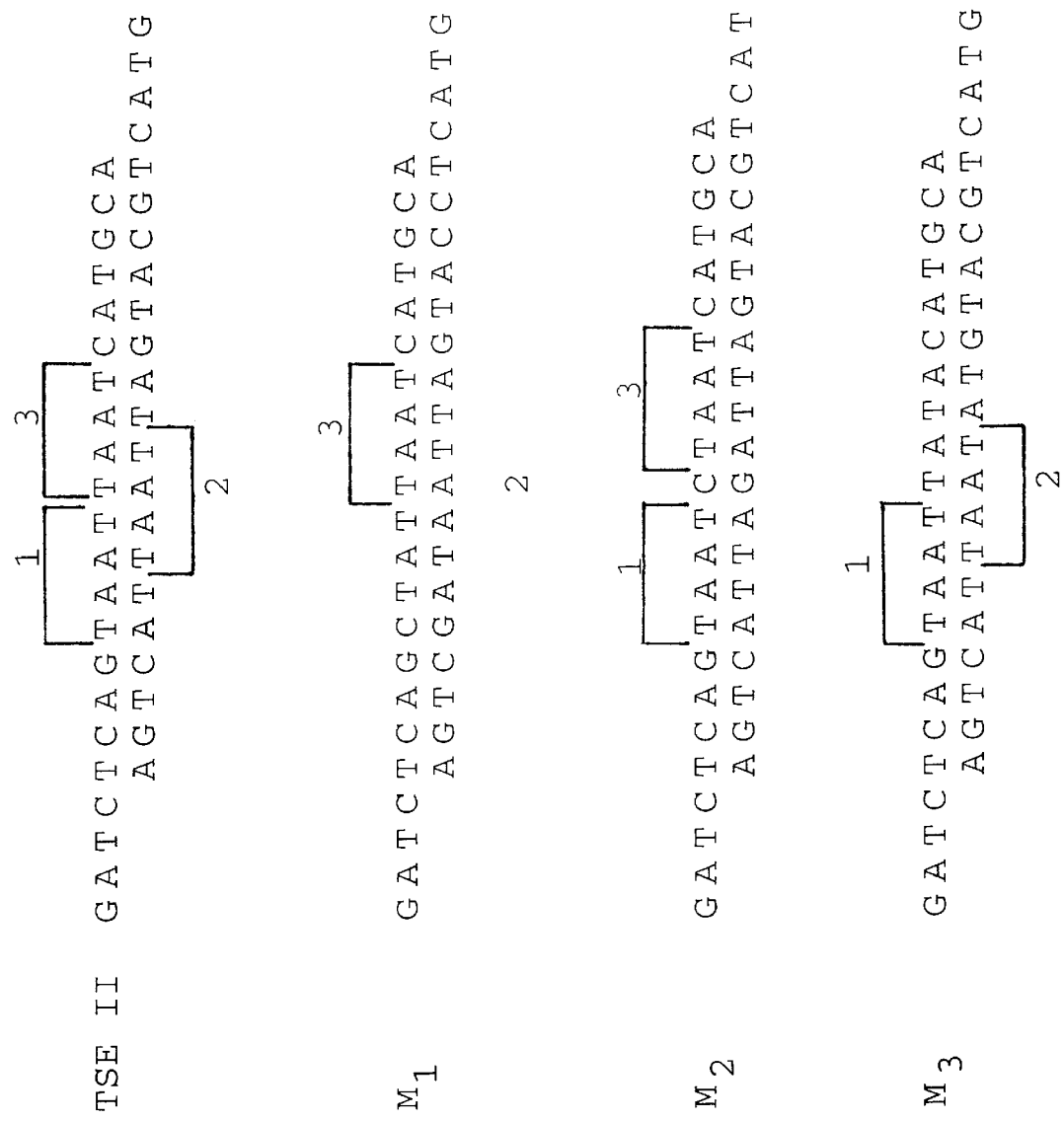

To determine whether Pbx and STF-1 can bind cooperatively to other STF-1 target sites besides TSEII, gel shift assays were performed with the recombinant STF-1 and Pbx proteins on the somatostatin TSEI or insulin P and Flat elements, sites which bind STF-1 and which are required for islet cell restricted expression of the rat somatostatin and insulin I genes, respectively, in pancreatic cells (FIG. 2D and FIG. 2E). In contrast to the TSEII element (FIG. 2D, lanes 1–4), no heteromeric STF-1-Pbx complex was observed on the TSEI, P or FLAT elements. Indeed, heteromeric STF-1 complexes are also undetectable when the TSEI, P, or FLAT elements are used in gel shift assays of crude pancreatic cell extracts (data not shown) (20).

Figure 2F:
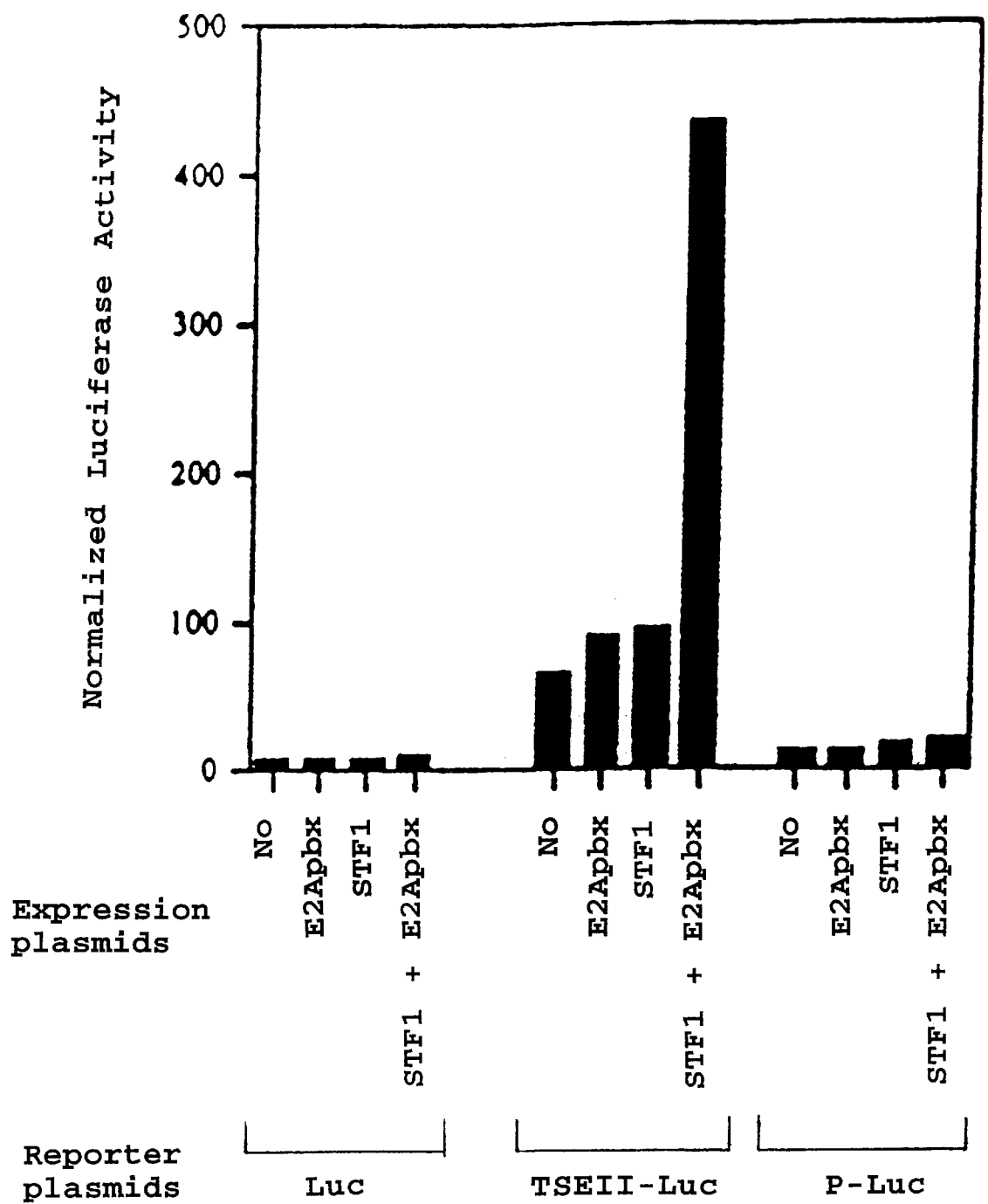

To determine whether STF-1 and Pbx can stimulate transcription in a cooperative manner, transient transfection assays were performed using a reporter vector which contains two copies of the somatostatin TSE II site upstream of a minimal growth hormone promoter (FIG. 2F). To optimize regulatory contributions from the transfected Pbx expression plasmid, an E2A-Pbx vector was employed which expresses the activation domain of E2A fused to Pbx (15). When transfected separately into GC cells, STF-1 and E2a-Pbx expression vectors had negligible effects on TSE II luciferase reporter activity. Co-transfection of STF-1 and E2a-Pbx effector plasmids markedly increased TSE II reporter activity, however, suggesting that STF-1 can indeed cooperate with Pbx on the TSE II site. By contrast, no such cooperativity between STF-1 and E2A-Pbx was observed using a reporter plasmid which contained the insulin P element (P-Luc). As the P-element was unable to form STF-1-Pbx heterodimers in DNA binding assays (FIG. 2D), these results demonstrate that STF-1 and Pbx can act synergistically on only a subset of sites which are able to recognize the STF-1-Pbx heterodimer.

To identify sequences within the somatostatin TSEII element which were important for Pbx-STF-1 cooperativity, several mutant TSEII oligonucleotides were constructed (FIG. 2D and FIG. 2E). The TSEII site contains 3 TAAT motifs, the principle recognition motif for homeodomain proteins. Mutation of TAAT motifs 1 or 3 (M1 and M3, plus strand) had minimal effects on cooperative binding between STF-1 and Pbx, but mutation of TAAT motif 2 (minus strand) completely abolished Pbx-STF-1 cooperativity, indicating the importance of that special TAAT motif for the STF-1-Pbx complex formation. Mutation in the third TAAT motif (M3) also affected formation of STF-1 monomeric C1 complex.

To identify residues in STF-1 which promote cooperative binding with Pbx, a series of truncated STF-1 polypeptides were examined in gel shift assays using the TSEII probe (FIG. 3A and FIG. 3B). Deletion of residues C-terminal to the homeobox domain had no effect on cooperative binding with Pbx ($\Delta$216-284 mutant). And N-terminally truncated STF-1 polypeptides lacking the STF-1 trans-activation domain (amino acid 1-115) also retained ability to bind cooperatively to the TSEII site. But further deletion of the residues from amino acid 115 to 123 abolished cooperativity with Pbx, suggesting that a region outside the STF-1 homeodomain was important for heterodimer formation (FIG. 3A and FIG. 3B). Indeed, the homeobox region of STF-1 (Hox 140-215) formed a monomeric complex on the TSEII site, but did not bind cooperatively with Pbx. STF-1 polypeptides containing N-terminal sequences in addition to the STF-1 homeodomain (amino acid 110-215) showed cooperativity with Pbx indicating that N-terminal residues flanking the STF-1 homeobox may form protein-protein contacts with Pbx upon binding to the TSEII site.

Figure 3C:
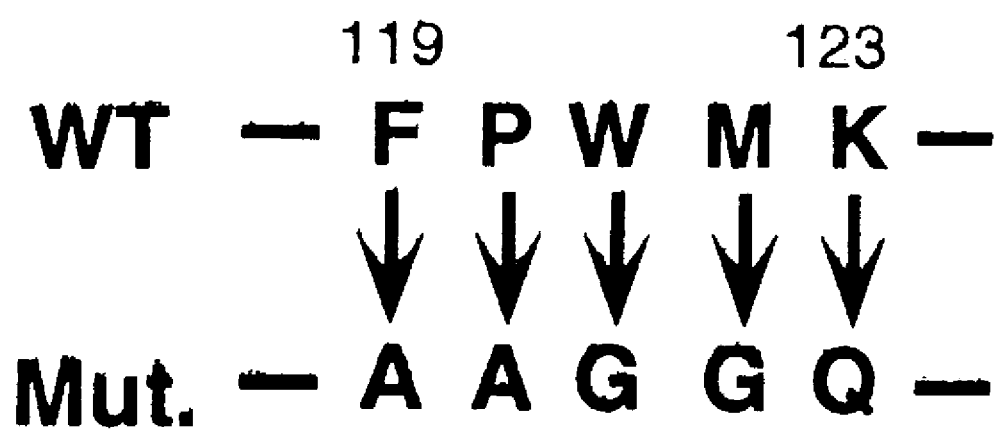
Figure 3D:
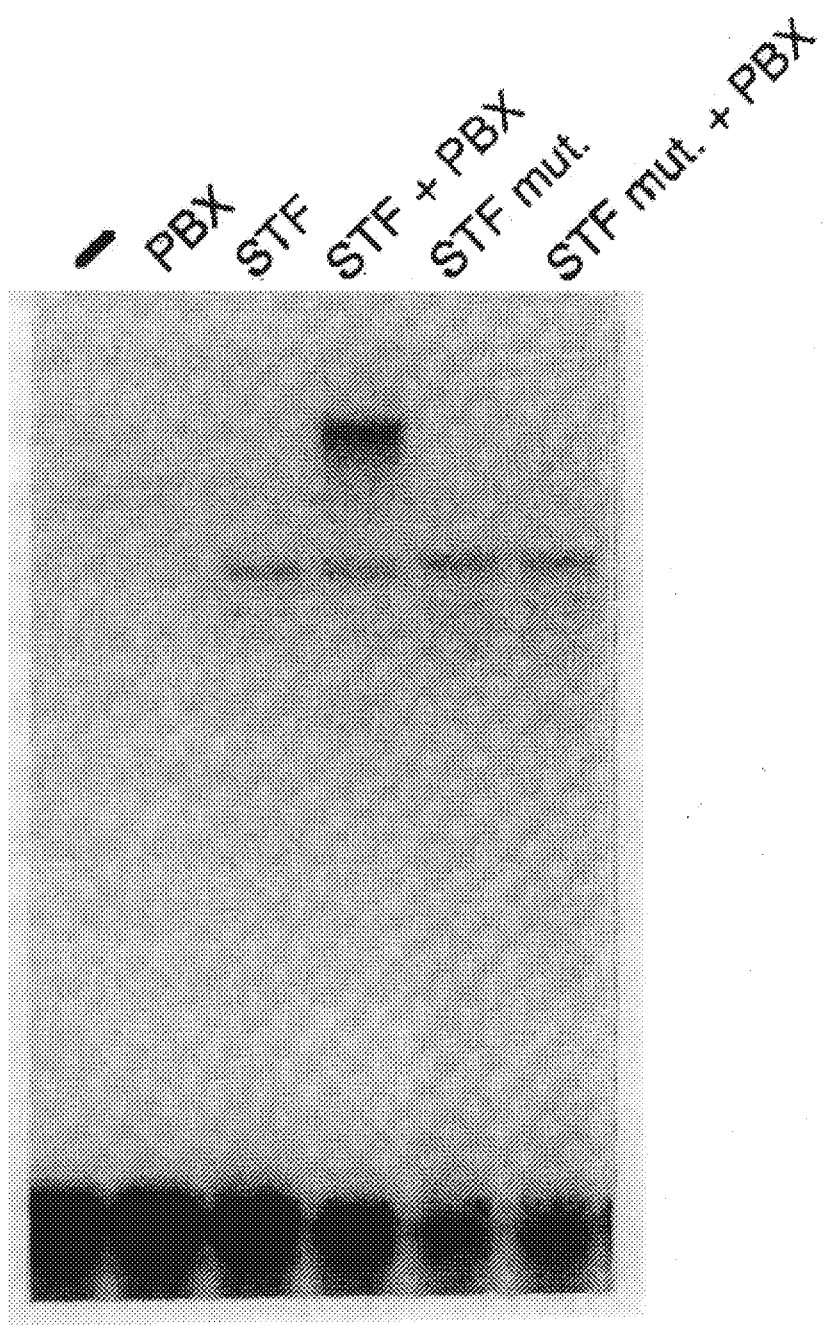
Figure 3E:
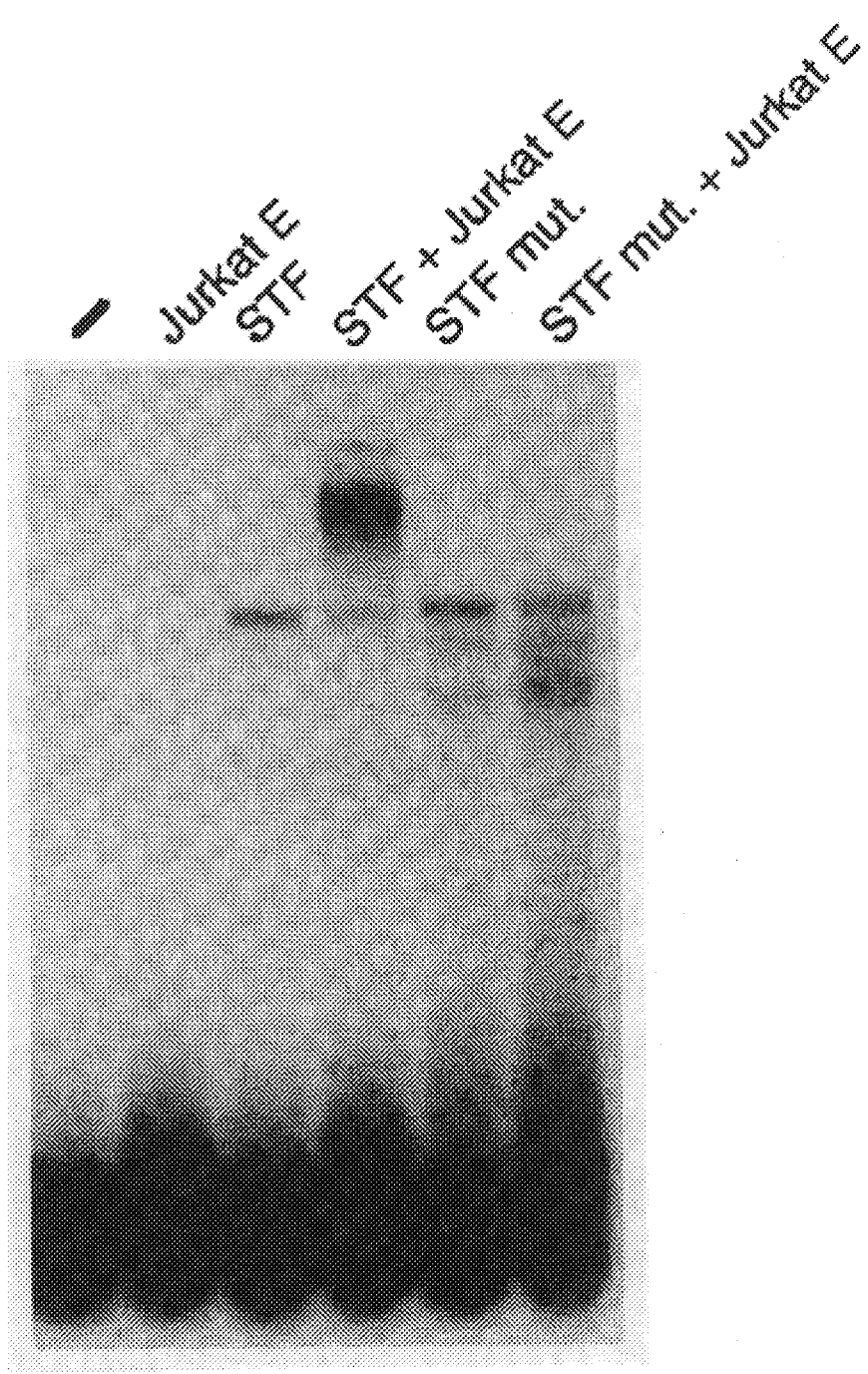

In the process of comparing residues in STF-1 with other Drosophila homeodomain proteins which bind cooperatively to DNA with extradenticle, the Drosophila homolog of Pbx, a pentapeptide motif FPWMK was noticed which is located within this N-terminal region of STF-1 (amino acid 115-123) and which is conserved in many homeoproteins from a wide variety of metazoans (5). To illustrate the importance of this peptide motif for cooperativity with Pbx, a mutant STF-1 cDNA was constructed containing amino acid substitutions at each residue in the motif (FPWMK to AAGGQ) (FIG. 3C). When compared with wild-type STF-1 protein in gel mobility shift assays, the mutated STF-1 protein was deficient in its ability to cooperate with either recombinant Pbx or with endogenous Pbx from Jurkat extracts (FIG. 3D and FIG. 3E, respectively). By contrast, the mutant STF-1 protein showed wild-type binding activity on insulin P and Flat elements, sites which do not form the heterodimeric complex. These results demonstrate that the Pbx interaction motif in STF-1, termed the PBX interaction motif region or pim, is indeed necessary for cooperativity with Pbx.

Figure 5B:
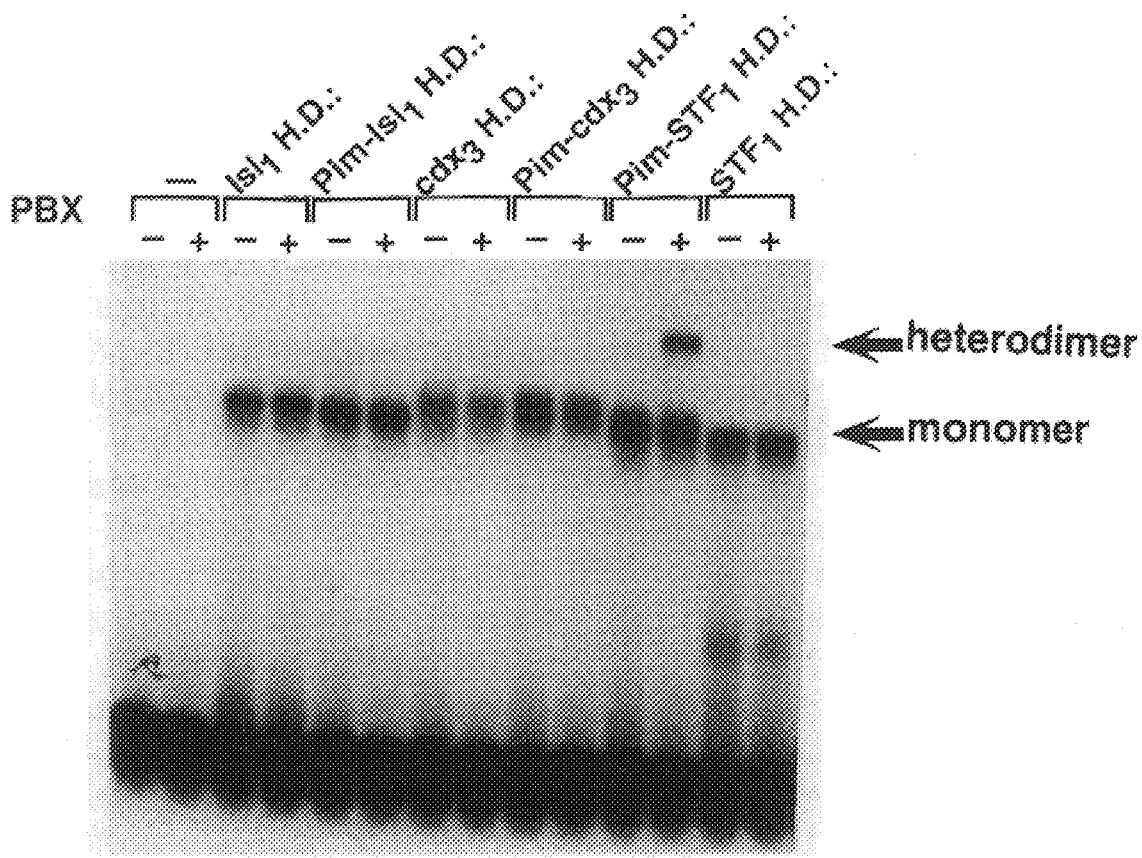

To determine whether the PBX interaction motif region was sufficient for cooperativity with Pbx, the ability of this motif to confer Pbx cooperativity when fused to heterologous homeobox proteins was examined (FIG. 5B). In gel mobility shift assays, the lim homeodomain protein Isl1 recognized the somatostatin TSEII site with high affinity but was unable to heterodimerize with Pbx. Remarkably, fusion of the PBX interaction motif region upstream of the Isl1 homeobox did not promote cooperativity with Pbx. The caudal-like factor cdx3 contains a PBX interaction motif related motif CEWMR upstream of its homeodomain. But, like Isl1, cdx3 does not heterodimerize with Pbx; and addition of the PBX interaction motif region to the cdx3 homeodomain did not promote Pbx cooperativity. Remarkably, the spacing between the PBX interaction motif region and the homeobox is comparable for STF-1 and both the PBX interaction motif-Isl1 and PBX interaction motif-cdx3 fusion proteins, suggesting that the distance from the homeobox domain may not explain their inability to cooperate with Pbx. Additionally, the chimeric proteins (PBX interaction motif-Isl1, PBX interaction motif-cdx3) appeared to bind DNA with wild-type affinity, indicating that lack of cooperativity may not reflect incorrect folding. Taken together, these results suggest that, although the PBX interaction motif region is required for formation of a heteromeric complex with Pbx, additional residues within the STF-1 homeodomain are required for cooperative binding to the somatostatin TSE II site.

Figure 6A:
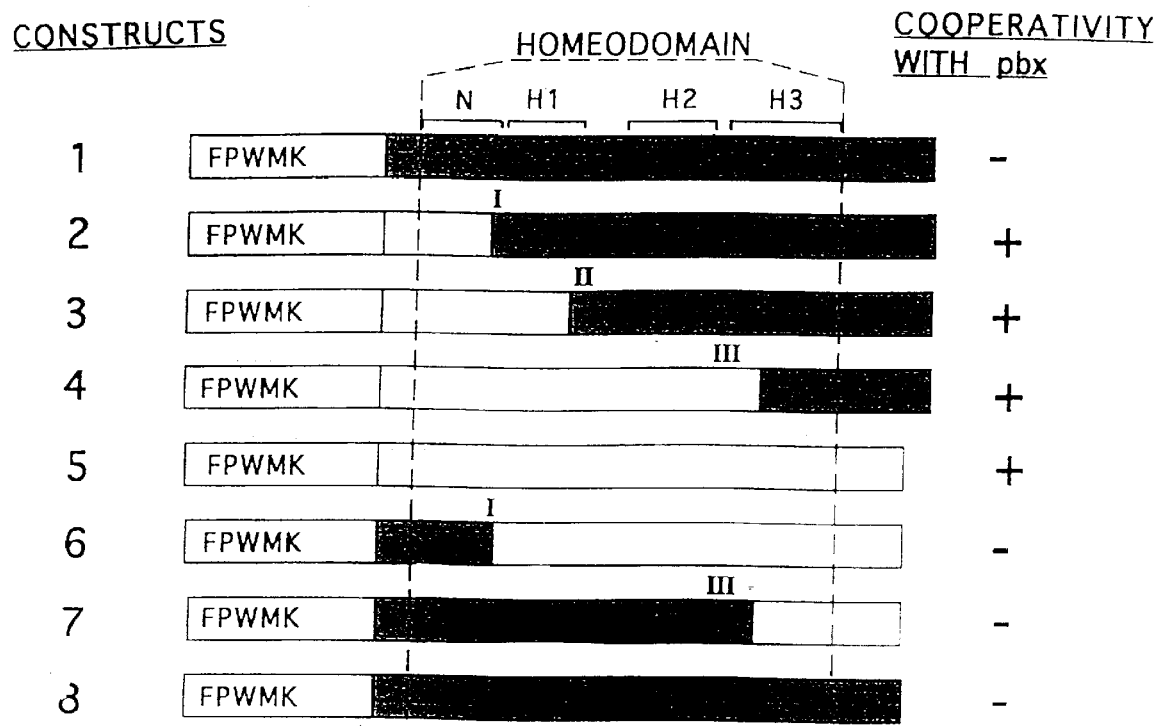
FIG. 6A–C shows the N-terminal arm of the STF-1 homeodomain is necessary for cooperativity with Pbx. Gel shift analysis of PBX interaction motif-cdx3 fusion constructs containing the STF-1 PBX interaction motif motif (amino acid residues 110–138) plus various regions of the STF-1 homeodomain substituted in place of the cdx3 homeodomain.
Figure 6B:
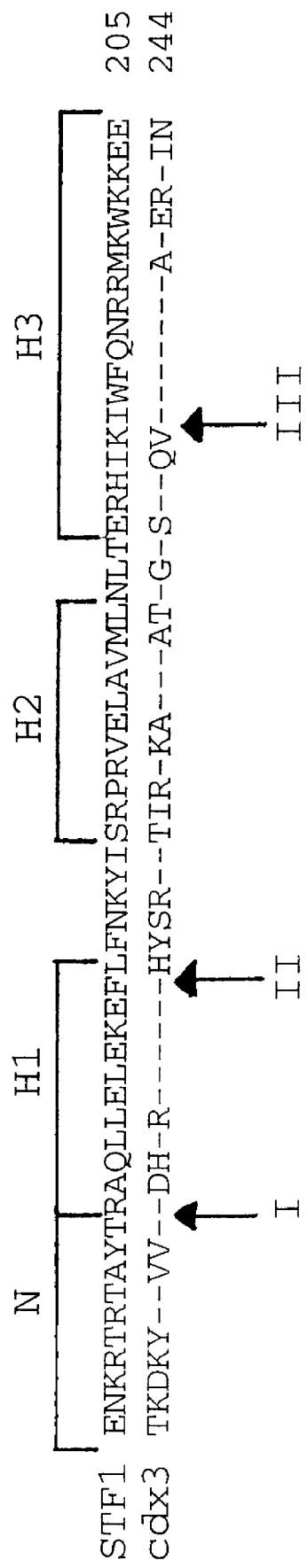
Figure 6C:
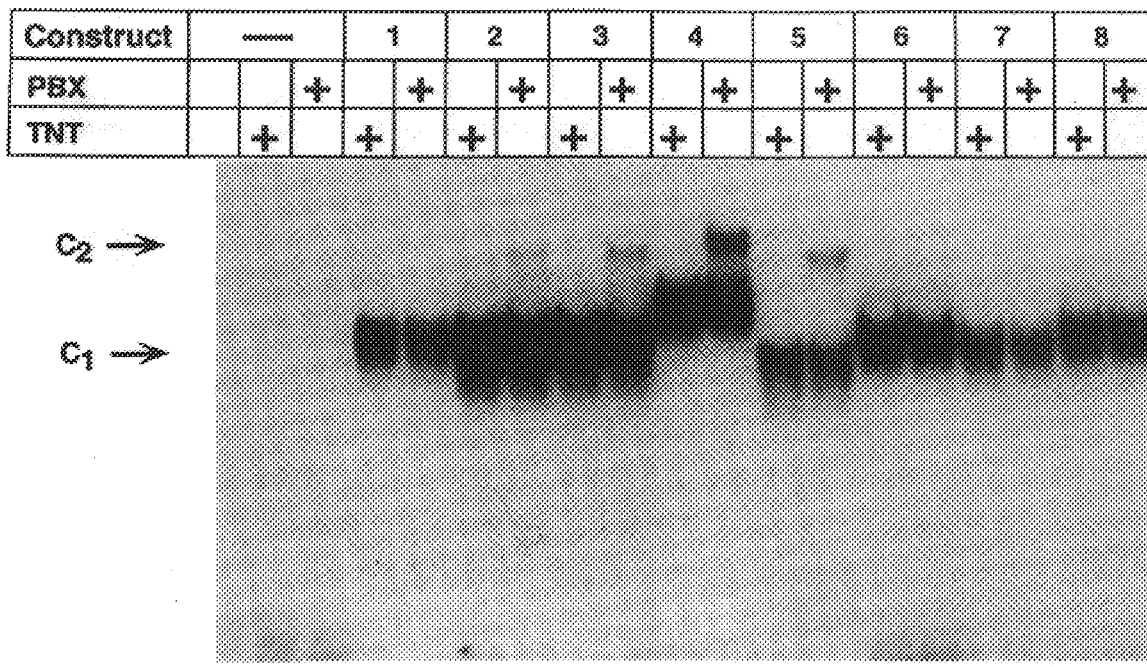

To characterize residues within the homeodomain of STF-1 which, in addition to the PBX interaction motif region, were functionally important for cooperative binding with Pbx, segments within the cdx3 homeodomain were replaced with the corresponding segments of STF-1 (FIG. 6C). Using the PBX interaction motif-cdx3 as fusion template for such experiments, it was determined that the N-terminal arm of STF-1 rescued cooperativity with Pbx, but other regions of the STF-1 homeodomain (helices 1, 2, or 3) showed no such activity. These results demonstrate that both the PBX interaction motif and the N-terminal arm of STF-1 are necessary for complex formation with Pbx.

Extradenticle, the Drosophila homolog of Pbx, appears to be essential for proper activation of a subset of target genes such as wingless, teashirt, and decapentaplegic during development (24). Extradenticle appears to induce these target genes by binding cooperatively to DNA with different homeotic proteins (2, 25). The present invention demonstrates that Pbx, the human homolog of extradenticle, forms a heterodimeric complex with STF-1 on the somatostatin TSEII element. Compared to STF-1 alone, the STF-1-Pbx complex is highly stable, as measured by the decreased off-rate of this complex in gel mobility shift assays. It is important to note, however, that these results do not discern between various members of the Pbx family (Pbx-1,2,3) all of which apparently have the capacity to bind cooperatively with HOX proteins.

Formation of a STF-1-Pbx heterodimer on the somatostatin TSEII site requires a pentapeptide motif (FPMWK) which is conserved in a number of homeotic proteins, not only in vertebrates, but also in Drosophila (5) and *C. elegans*. Thus the *C. elegans* homeotic proteins mab5 or lin-39, which contain this motif, may similarly cooperate with the protein ceh-20, which appears homologous to Pbx (1). Using an artificial target sequence to induce Pbx:hox heterodimer formation, Chang et al. have noted the importance of this conserved motif for cooperative binding with Pbx to DNA (3). These results suggest that the effects of Pbx are not restricted to proteins in the hox complex, but include orphan homeobox proteins such as STF- 1.

Although Chang et al. found that fusion of the conserved YPMWK motif to Hox A10 was sufficient to promote cooperativity with Pbx (3), no induction of cooperativity was seen when this motif was transferred to islet cell homeodomain proteins such as isl-1 and cdx-3. These results indicated that additional residues within the homeodomain itself may be required for formation of the STF-1/Pbx complex. In this regard, it was found that the flexible N terminal arm of the STF-1 homeodomain (amino acids 145–153) was essential for cooperativity with Pbx. The N-terminal arm has been shown confer functional specificity to homeodomain proteins such as Antennapedia, although the underlying mechanism remains uncharacterized (4; 26). Structural studies have revealed that the N-terminal arm is located within the minor groove of the DNA where it may impart subtle differences in DNA binding or in protein-protein interactions. Although these results do not discriminate between these models, it is tempting to speculate that the formation of a STF-1/Pbx complex may rely in part on the ability of the N-terminal arm to form specific minor groove contacts.

Formation of the STF-1-Pbx heterodimer occurs on only a subset of potential STF-1 target sites. These results suggest that this preference may form the basis for target site selection in developing islet cells. It was previously noted, for example, that STF-1 induces both insulin and somatostatin expression, albeit in distinct cell types (β and δ, respectively) within the pancreatic islet. In β cells, STF-1 appears to induce insulin expression by acting cooperatively with the helix loop helix protein E47. By contrast, STF-1 appears to promote somatostatin expression in δ cells by binding cooperatively to the TSEII site with Pbx. These observations suggest that the commitment of cells within the islet lineage to express either insulin or somatostatin may depend on the relative expression of E box binding versus Pbx type proteins.

A combinatorial mechanism for developmental regulation, like the one envisioned here for pancreatic development, has also been described in yeast. In this regard, the homeodomain protein Matα2 cooperates with Matα1 in diploid a/α cells to bind hsg operators and to repress haploid-specific genes. But in haploid a or α cells, Matα2 appears to cooperate with a different activator, MCM1, and to thereby activate a distinct genetic program (9).

The presence of a conserved motif which permits interaction between Pbx and certain homeobox proteins may explain in part the global effects of this regulator in development. The somatostatin gene is expressed in a number of tissues besides pancreas including brain, stomach, and medullary thyroid. Although factors which direct somatostatin expression in these tissues have not been identified, these results predict that such proteins may stimulate somatostatin expression on the TSEII element by forming heterodimeric complexes with Pbx.

The following references were cited herein:
1. Burglin T. R. et al., *Nature Genet.* 1:319–320, 1992.
2. Chan S. et al., *Cell* 78:603–615, 1994.
3. Chang C. et al., *Genes & Dev.* 9:663–674, 1995.
4. Furukubo-Tokunaga K. et al., *Proc. Natl. Acad. Sci.* 90:6360 . 6364, 1993.
5. Gehring W. J. et al., *Annu. Rev. Biochem.* 63:437–526, 1994.
6. German M. S. et al., *Genes & Dev.* 6:2165–2176, 1992.
7. Guz Y. et al., *Development* 121:11–18, 1995.
8. Hayashi S. et al., *Cell* 63:883–894, 1990.
9. Johnson A., Acombinatorial regulatory circuit in budding yeast., In S. McKnight (ed.), transcriptional regulation, Cold Spring Harbor Lab. Press, N.Y., p.975–1006, 1992.
10. Jonsson J. et al., *Nature* 371:606–609, 1994.
11. Kamps M. P. et al., *Genes & Dev.* 5:358–368, 1991.
12. Karlsson O. et al., *Nature* 344:879–882, 1990.
13. Krumlauf R., *Cell* 78:191–201, 1994.
14. Leonard J. et al., *Mol. Endocrinol.* 7:1275–1283, 1993.
15. Lu Q. et al., *Mol. Cell. Biol.* 14:3938–3948, 1994.
16. McGinnis W. et al., *Cell* 68:283–302, 1992.
17. Miller C. P. et al., *EMBO J.* 13:1145–1156, 1994.
18. Monica K. et al., *Mol. Cell. Biol.* 11:6149–6157, 1991.
19. Ohlsson H. et al., *EMBO J.* 12:4251–4259, 1993.
20. Peers B. et al., *Mol. Endocrinol.* 8:1798–1806, 1994.
21. Peifer M. et al., *Genes & Dev.* 4:1209–1223, 1990.
22. Peshavaria M. et al., *Mol. Endocrinol.* 8:806–816, 1994.
23. Rauskolb C., et al., *Cell* 74:1101–1112, 1993.
24. Rauskolb C., et al., *EMBO J.* 13:3561–3569, 1994.
25. van Dijk M., et al., *Cell* 78:616–624, 1994.
26. Zeng W., et al., *Development* 118:339–352, 1993.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A DNA binding assay to determine compounds effective for promoting somatostatin-transcription factor-1 binding to an STF-1 binding site, comprising the steps of:

combining end-labeled, double-stranded DNA having an STF-1 binding site with STF-1 as a control in a first container;

combining end-labeled, double-stranded DNA having an STF-1 binding site with STF-1 and a test compound as a sample in a second container;

incubating said first and second containers;

loading said control and said sample onto an electrophoresis gel;

applying an electrical current to said electrophoresis gel so as to cause said control and said sample to migrate within said gel;

detecting said control and said sample;

comparing migration of said control to migration of said sample, wherein if said sample has a slower migration than said control, said test compound is effective in promoting STF-1 binding to said STF-1 binding site.

2. The assay of claim 1, wherein a second sample is prepared containing end-labeled, double-stranded DNA having an somatostatin-transcription factor-1 binding site; STF-1; a test compound; and excess, unlabeled double-stranded DNA having the same sequence as said end-labeled, double-stranded DNA, wherein if detection of said second sample results in a decrease in labeled DNA/STF-1/test compound complex, binding of said STF-1/test compound complex is specific for said double-stranded DNA having an STF-1 binding site.

3. The assay of claim 1, wherein said end-labelled double-stranded DNA has one strand having the sequence of SEQ ID No. 1 and the other strand having the sequence of SEQ ID No. 2.

4. A DNA binding assay to determine compounds effective for promoting somatostatin-transcription factor-1 binding to an STF-1 binding site, comprising the steps of:

transfecting a first expression plasmid that consistuitively expresses STF-1 and a second expression plasmid that expresses a reporter gene under the control of an STF-1 binding site into an appropriate cell line;

transfecting a third plasmid into said transfected appropriate cell line, said third expression plasmid expressing a test compound;

measuring an amount of transcription of said reporter gene, wherein if said transcription takes place, said test compound is effective for promoting STF-1 binding to said STF-1 binding site.

5. The assay of claim 4, wherein said second expression plasmid contains a copy of a somatostatin TSE II site as said somatostatin-transcription factor-1 binding site.

6. The assay of claim 4, wherein said appropriate cell line is GC cells.

* * * * *

UNITED STATES PATENT AND TRADEMARK OFFICE
CERTIFICATE OF CORRECTION

PATENT : 5,849,493  
DATED : December 1, 1998  
INVENTOR(S): Marc Montminy and Bernard Peers Page 1 of 2

It is certified that error appears in the above-identified patent and that said Letters Patent is hereby corrected as shown below:

In Column 1, line 22, please insert the word --by-- between the words "characterized" and "primansulia".

In Column 2, line 3, please insert the word --in-- between the words "present" and "rat".

In Column 8, line 6, please delete the word "tis".

In Column 8, line 55, "RNApolymerase" should read --RNA polymerase--.

In Column 8, line 62, "mdia" should read --media--.

In Column 9, line 17, please insert the word --the-- between the words "temperature," and "source".

In Column 9, line 18, "use the method" should read --the method used--.

In Column 9, line 55, "monnon" should read --common--.

In Column 15, line 45, please insert the word --to-- between the words "shown" and "confer".

In Column 35, line 25, "an" should read --a--.

UNITED STATES PATENT AND TRADEMARK OFFICE
CERTIFICATE OF CORRECTION

PATENT : 5,849,493
DATED : December 1, 1998
INVENTOR(S): Marc Montminy and Bernard Peers It is certified that error appears in the above-identified patent and that said Letters Patent is hereby corrected as shown below:

In Column 36, line 11, "consistuitively" should read --constituitively--.

In Column 36, lines 16-17, please delete the word "appropriate".

Signed and Sealed this

First Day of May, 2001

Attest:

NICHOLAS P. GODICI

*Attesting Officer*     *Acting Director of the United States Patent and Trademark Office*

SEQUENCE LISTING ( 1 ) GENERAL INFORMATION:

( i i i ) NUMBER OF SEQUENCES: 31

( 2 ) INFORMATION FOR SEQ ID NO:1:

( i ) SEQUENCE CHARACTERISTICS:
        ( A ) LENGTH: 22 bp
        ( B ) TYPE: nucleic acid
        ( C ) STRANDEDNESS: double
        ( D ) TOPOLOGY: linear ( i i ) MOLECULE TYPE:
        ( A ) DESCRIPTION: other nucleic acid ( i i i ) HYPOTHETICAL: No ( i v ) ANTI-SENSE: No ( v i ) ORIGINAL SOURCE:

( x i ) SEQUENCE DESCRIPTION: SEQ ID NO:1:

GATCTCAGTA ATTAATCATG CA                22

( 2 ) INFORMATION FOR SEQ ID NO: 2:

( i ) SEQUENCE CHARACTERISTICS:
        ( A ) LENGTH: 22 bp
        ( B ) TYPE: nucleic acid
        ( C ) STRANDEDNESS: double
        ( D ) TOPOLOGY: linear ( i i ) MOLECULE TYPE:
        ( A ) DESCRIPTION: other nucleic acid ( i i i ) HYPOTHETICAL: No ( i v ) ANTI-SENSE: No ( v i ) ORIGINAL SOURCE:

( x i ) SEQUENCE DESCRIPTION: SEQ ID NO: 2:

AGTCATTAAT TAGTACGTCA TG                22

( 2 ) INFORMATION FOR SEQ ID NO:3:

( i ) SEQUENCE CHARACTERISTICS:
        ( A ) LENGTH: 22
        ( B ) TYPE: nucleic acid
        ( C ) STRANDEDNESS: double
        ( D ) TOPOLOGY: linear ( i i ) MOLECULE TYPE:
        ( A ) DESCRIPTION: other nucleic acid ( i i i ) HYPOTHETICAL: No ( i v ) ANTI-SENSE: No ( v i ) ORIGINAL SOURCE:

( x i ) SEQUENCE DESCRIPTION: SEQ ID NO: 3:

GATCTCAGC TATTAATCATG CA                22

( 2 ) INFORMATION FOR SEQ ID NO:4:

( i ) SEQUENCE CHARACTERISTICS:
        ( A ) LENGTH: 22 bp
        ( B ) TYPE: nucleic acid
        ( C ) STRANDEDNESS: double (D) TOPOLOGY: linear (ii) MOLECULE TYPE:
(A) DESCRIPTION: other nucleic acid (iii) HYPOTHETICAL: No (iv) ANTI-SENSE: No (vi) ORIGINAL SOURCE:

(xi) SEQUENCE DESCRIPTION: SEQ ID NO: 4:

AGTCGATAAT TAGTACCTCA TC 22

(2) INFORMATION FOR SEQ ID NO:5:

(i) SEQUENCE CHARACTERISTICS:
(A) LENGTH: 23
(B) TYPE: nucleic acid
(C) STRANDEDNESS: double
(D) TOPOLOGY: linear (ii) MOLECULE TYPE:
(A) DESCRIPTION: other nucleic acid (iii) HYPOTHETICAL: No (iv) ANTI-SENSE: No (vi) ORIGINAL SOURCE:

(xi) SEQUENCE DESCRIPTION: SEQ ID NO: 5:

GATCTCAGTA ATCTAATCAT GCA 23

(2) INFORMATION FOR SEQ ID NO:6:

(i) SEQUENCE CHARACTERISTICS:
(A) LENGTH: 22
(B) TYPE: nucleic acid
(C) STRANDEDNESS: double
(D) TOPOLOGY: linear (ii) MOLECULE TYPE:
(A) DESCRIPTION: other nucleic acid (iii) HYPOTHETICAL: No (iv) ANTI-SENSE: No (vi) ORIGINAL SOURCE:

(xi) SEQUENCE DESCRIPTION: SEQ ID NO: 6:

AGTCATTAAT ATGTACGTCA TG 22

(2) INFORMATION FOR SEQ ID NO:7:

(i) SEQUENCE CHARACTERISTICS:
(A) LENGTH: 22 bp
(B) TYPE: nucleic acid
(C) STRANDEDNESS: double
(D) TOPOLOGY: linear (ii) MOLECULE TYPE:
(A) DESCRIPTION: other nucleic acid (iii) HYPOTHETICAL: No (iv) ANTI-SENSE: No (vi) ORIGINAL SOURCE:

(xi) SEQUENCE DESCRIPTION: SEQ ID NO: 7:

GATCTCAGTA ATTATACATG CA 22

( 2 ) INFORMATION FOR SEQ ID NO:8:

( i ) SEQUENCE CHARACTERISTICS:
    ( A ) LENGTH: 22 bp
    ( B ) TYPE: nucleic acid
    ( C ) STRANDEDNESS: double
    ( D ) TOPOLOGY: linear ( i i ) MOLECULE TYPE:
    ( A ) DESCRIPTION: other nucleic acid ( i i i ) HYPOTHETICAL: No ( i v ) ANTI-SENSE: No ( v i ) ORIGINAL SOURCE:

( x i ) SEQUENCE DESCRIPTION: SEQ ID NO: 8:

AGTCATTAAT ATGTACGTCA TG    22

( 2 ) INFORMATION FOR SEQ ID NO:9:

( i ) SEQUENCE CHARACTERISTICS:
    ( A ) LENGTH: 25 bp
    ( B ) TYPE: nucleic acid
    ( C ) STRANDEDNESS: double
    ( D ) TOPOLOGY: linear ( i i ) MOLECULE TYPE:
    ( A ) DESCRIPTION: other nucleic acid ( i i i ) HYPOTHETICAL: No ( i v ) ANTI-SENSE: No ( v i ) ORIGINAL SOURCE:

( x i ) SEQUENCE DESCRIPTION: SEQ ID NO: 9:

GATCTAGAGC CCTTAATGGG CCAAA    25

( 2 ) INFORMATION FOR SEQ ID NO:10:

( i ) SEQUENCE CHARACTERISTICS:
    ( A ) LENGTH: 25 bp
    ( B ) TYPE: nucleic acid
    ( C ) STRANDEDNESS: double
    ( D ) TOPOLOGY: linear ( i i ) MOLECULE TYPE:
    ( A ) DESCRIPTION: other nucleic acid ( i i i ) HYPOTHETICAL: No ( i v ) ANTI-SENSE: No ( v i ) ORIGINAL SOURCE:

( x i ) SEQUENCE DESCRIPTION: SEQ ID NO: 10:

ATCTCGGGAA TTACCCGGTT TCTAG    25

( 2 ) INFORMATION FOR SEQ ID NO:11:

( i ) SEQUENCE CHARACTERISTICS:
    ( A ) LENGTH: 23 bp
    ( B ) TYPE: nucleic acid
    ( C ) STRANDEDNESS: double
    ( D ) TOPOLOGY: linear ( i i ) MOLECULE TYPE:
    ( A ) DESCRIPTION: other nucleic acid ( i i i ) HYPOTHETICAL: No (iv) ANTI-SENSE: No (vi) ORIGINAL SOURCE:

(xi) SEQUENCE DESCRIPTION: SEQ ID NO: 11:

GATCTTGCGA GGCTAATGGT GCG 23

(2) INFORMATION FOR SEQ ID NO:12:

(i) SEQUENCE CHARACTERISTICS:
        (A) LENGTH: 23 bp
        (B) TYPE: nucleic acid
        (C) STRANDEDNESS: double
        (D) TOPOLOGY: linear (ii) MOLECULE TYPE:
        (A) DESCRIPTION: other nucleic acid (iii) HYPOTHETICAL: No (iv) ANTI-SENSE: No (vi) ORIGINAL SOURCE:

(xi) SEQUENCE DESCRIPTION: SEQ ID NO: 12:

AACGCTCCGA TTACCACGCC ATG 23

(2) INFORMATION FOR SEQ ID NO:13:

(i) SEQUENCE CHARACTERISTICS:
        (A) LENGTH: 28 bp
        (B) TYPE: nucleic acid
        (C) STRANDEDNESS: double
        (D) TOPOLOGY: linear (ii) MOLECULE TYPE:
        (A) DESCRIPTION: other nucleic acid (iii) HYPOTHETICAL: No (iv) ANTI-SENSE: No (vi) ORIGINAL SOURCE:

(xi) SEQUENCE DESCRIPTION: SEQ ID NO: 13:

GATCTTGTTA ATAATCTAAT TACCCTAG 28

(2) INFORMATION FOR SEQ ID NO:14:

(i) SEQUENCE CHARACTERISTICS:
        (A) LENGTH: 27 bp
        (B) TYPE: nucleic acid
        (C) STRANDEDNESS: double
        (D) TOPOLOGY: linear (ii) MOLECULE TYPE:
        (A) DESCRIPTION: other nucleic acid (iii) HYPOTHETICAL: No (iv) ANTI-SENSE: No (vi) ORIGINAL SOURCE:

(xi) SEQUENCE DESCRIPTION: SEQ ID NO: 14:

AACAATTATT AGATTAATGG GATCCAT 27

(2) INFORMATION FOR SEQ ID NO:15:

(i) SEQUENCE CHARACTERISTICS:
        (A) LENGTH: 5 amino acids (B) TYPE: amino acid
            (C) STRANDEDNESS: single
            (D) TOPOLOGY: linear (ii) MOLECULE TYPE:
            (A) DESCRIPTION: peptide (iii) HYPOTHETICAL: No (iv) ANTI-SENSE: No (vi) ORIGINAL SOURCE:

(xi) SEQUENCE DESCRIPTION: SEQ ID NO: 15:

Phe Pro Trp Met Lys
                  5

(2) INFORMATION FOR SEQ ID NO: 16:

(i) SEQUENCE CHARACTERISTICS:
            (A) LENGTH: 23 nucleic acids
            (B) TYPE: nucleic acid
            (C) STRANDEDNESS: double
            (D) TOPOLOGY: linear (ii) MOLECULE TYPE:
            (A) DESCRIPTION: other nucleic acid (iii) HYPOTHETICAL: No (iv) ANTI-SENSE: No (vi) ORIGINAL SOURCE:

(xi) SEQUENCE DESCRIPTION: SEQ ID NO: 16:

AACGCTCCGA TTACCACGCC ATG                                                              23

(2) INFORMATION FOR SEQ ID NO:17:

(i) SEQUENCE CHARACTERISTICS:
            (A) LENGTH: 28 nucleic acids
            (B) TYPE: nucleic acid
            (C) STRANDEDNESS: double
            (D) TOPOLOGY: linear (ii) MOLECULE TYPE:
            (A) DESCRIPTION: other nucleic acid (iii) HYPOTHETICAL: No (iv) ANTI-SENSE: No (vi) ORIGINAL SOURCE:

(xi) SEQUENCE DESCRIPTION: SEQ ID NO: 17:

GATCTTGTTA ATAATCTAAT TACCCTAG                                                         28

(2) INFORMATION FOR SEQ ID NO:18:

(i) SEQUENCE CHARACTERISTICS:
            (A) LENGTH: 28 nucleic acids
            (B) TYPE: nucleic acid
            (C) STRANDEDNESS: double
            (D) TOPOLOGY: linear (ii) MOLECULE TYPE:
            (A) DESCRIPTION: other nucleic acid (iii) HYPOTHETICAL: No (iv) ANTI-SENSE: No (vi) ORIGINAL SOURCE:

( x i ) SEQUENCE DESCRIPTION: SEQ ID NO: 18:

AACAATTATT AGATTAATGG GATCCATC 28

( 2 ) INFORMATION FOR SEQ ID NO:19:

( i ) SEQUENCE CHARACTERISTICS:
        ( A ) LENGTH: 5 amino acids
        ( B ) TYPE: amino acid
        ( C ) STRANDEDNESS:
        ( D ) TOPOLOGY: linear ( i i ) MOLECULE TYPE:
        ( A ) DESCRIPTION: protein ( i i i ) HYPOTHETICAL: No ( i v ) ANTI-SENSE: No ( v i ) ORIGINAL SOURCE:

( x i ) SEQUENCE DESCRIPTION: SEQ ID NO: 19:

Tyr Lys Trp Met Gln
                    5

( 2 ) INFORMATION FOR SEQ ID NO:20:

( i ) SEQUENCE CHARACTERISTICS:
        ( A ) LENGTH: 5 amino acid
        ( B ) TYPE: amino acid
        ( C ) STRANDEDNESS:
        ( D ) TOPOLOGY: linear ( i i ) MOLECULE TYPE:
        ( A ) DESCRIPTION: protein ( i i i ) HYPOTHETICAL: No ( i v ) ANTI-SENSE: No ( v i ) ORIGINAL SOURCE:

( x i ) SEQUENCE DESCRIPTION: SEQ ID NO: 20:

Tyr Pro Trp Met Lys
                    5

( 2 ) INFORMATION FOR SEQ ID NO:21:

( i ) SEQUENCE CHARACTERISTICS:
        ( A ) LENGTH: 5 amino acids
        ( B ) TYPE: amino acid
        ( C ) STRANDEDNESS:
        ( D ) TOPOLOGY: linear ( i i ) MOLECULE TYPE:
        ( A ) DESCRIPTION: protein ( i i i ) HYPOTHETICAL: No ( i v ) ANTI-SENSE: No ( v i ) ORIGINAL SOURCE:

( x i ) SEQUENCE DESCRIPTION: SEQ ID NO: 21:

Tyr Pro Trp Met Arg
                    5

( 2 ) INFORMATION FOR SEQ ID NO:22:

( i ) SEQUENCE CHARACTERISTICS:
        ( A ) LENGTH: 5 amino acids
        ( B ) TYPE: amino acid
        ( C ) STRANDEDNESS:

(D) TOPOLOGY: linear (ii) MOLECULE TYPE:
(A) DESCRIPTION: protein (iii) HYPOTHETICAL: No (iv) ANTI-SENSE: No (vi) ORIGINAL SOURCE:

(xi) SEQUENCE DESCRIPTION: SEQ ID NO: 22:

Tyr Pro Trp Met Ala
                  5

(2) INFORMATION FOR SEQ ID NO:23:

(i) SEQUENCE CHARACTERISTICS:
(A) LENGTH: 5 amino acids
(B) TYPE: amino acid
(C) STRANDEDNESS:
(D) TOPOLOGY: linear (ii) MOLECULE TYPE:
(A) DESCRIPTION: protein (iii) HYPOTHETICAL: No (iv) ANTI-SENSE: No (vi) ORIGINAL SOURCE:

(xi) SEQUENCE DESCRIPTION: SEQ ID NO: 23:

Tyr Pro Trp Met Thr
                  5

(2) INFORMATION FOR SEQ ID NO:24:

(i) SEQUENCE CHARACTERISTICS:
(A) LENGTH: 5 amino acids
(B) TYPE: amino acid
(C) STRANDEDNESS:
(D) TOPOLOGY: linear (ii) MOLECULE TYPE:
(A) DESCRIPTION: protein (iii) HYPOTHETICAL: No (iv) ANTI-SENSE: No (vi) ORIGINAL SOURCE:

(xi) SEQUENCE DESCRIPTION: SEQ ID NO: 24:

Phe Asp Trp Met Lys
                  5

(2) INFORMATION FOR SEQ ID NO: 25:

(i) SEQUENCE CHARACTERISTICS:
(A) LENGTH: 5 amino acids
(B) TYPE: amino acid
(C) STRANDEDNESS:
(D) TOPOLOGY: linear (ii) MOLECULE TYPE:
(A) DESCRIPTION: protein (iii) HYPOTHETICAL: No (iv) ANTI-SENSE: No (vi) ORIGINAL SOURCE:

( x i ) SEQUENCE DESCRIPTION: SEQ ID NO: 25:

Phe Pro Trp Met Lys
                    5

( 2 ) INFORMATION FOR SEQ ID NO:26:

( i ) SEQUENCE CHARACTERISTICS:
        ( A ) LENGTH: 5 amino acids
        ( B ) TYPE: amino acid
        ( C ) STRANDEDNESS:
        ( D ) TOPOLOGY: linear ( i i ) MOLECULE TYPE:
        ( A ) DESCRIPTION: protein ( i i i ) HYPOTHETICAL: No ( i v ) ANTI-SENSE: No ( v i ) ORIGINAL SOURCE:

( x i ) SEQUENCE DESCRIPTION: SEQ ID NO: 26:

Tyr Pro Trp Met Gln
                    5

( 2 ) INFORMATION FOR SEQ ID NO:27:

( i ) SEQUENCE CHARACTERISTICS:
        ( A ) LENGTH: 5 amino acids
        ( B ) TYPE: amino acid
        ( C ) STRANDEDNESS:
        ( D ) TOPOLOGY: linear ( i i ) MOLECULE TYPE:
        ( A ) DESCRIPTION: protein ( i i i ) HYPOTHETICAL: No ( i v ) ANTI-SENSE: No ( v i ) ORIGINAL SOURCE:

( x i ) SEQUENCE DESCRIPTION: SEQ ID NO: 27:

Phe Pro Trp Met Arg
                    5

( 2 ) INFORMATION FOR SEQ ID NO:28:

( i ) SEQUENCE CHARACTERISTICS:
        ( A ) LENGTH: 5 amino acids
        ( B ) TYPE: amino acid
        ( C ) STRANDEDNESS:
        ( D ) TOPOLOGY: linear ( i i ) MOLECULE TYPE:
        ( A ) DESCRIPTION: protein ( i i i ) HYPOTHETICAL: No ( i v ) ANTI-SENSE: No ( v i ) ORIGINAL SOURCE:

( x i ) SEQUENCE DESCRIPTION: SEQ ID NO: 28:

Tyr Ala Trp Met Arg
                    5

( 2 ) INFORMATION FOR SEQ ID NO:29:

( i ) SEQUENCE CHARACTERISTICS:
        ( A ) LENGTH: 5 amino acids
        ( B ) TYPE: amino acid (C) STRANDEDNESS:
(D) TOPOLOGY: linear (ii) MOLECULE TYPE:
(A) DESCRIPTION: protein (iii) HYPOTHETICAL: No (iv) ANTI-SENSE: No (vi) ORIGINAL SOURCE:

(xi) SEQUENCE DESCRIPTION: SEQ ID NO: 29:

Cys Glu Trp Met Arg
                 5

(2) INFORMATION FOR SEQ ID NO:30:

(i) SEQUENCE CHARACTERISTICS:
(A) LENGTH: 61 amino acids
(B) TYPE: amino acid
(C) STRANDEDNESS:
(D) TOPOLOGY: linear (ii) MOLECULE TYPE:
(A) DESCRIPTION: protein (iii) HYPOTHETICAL: No (iv) ANTI-SENSE: No (vi) ORIGINAL SOURCE:

(xi) SEQUENCE DESCRIPTION: SEQ ID NO: 30:

Glu Asn Lys Arg Thr Arg Thr Ala Tyr Thr Arg Ala Gln Leu Leu
                 5                  10                  15
Glu Leu Glu Lys Glu Phe Leu Phe Asn Lys Tyr Ile Ser Arg Pro
                20                  25                  30
Arg Arg Val Glu Leu Ala Val Met Leu Asn Leu Thr Glu Arg His
                35                  40                  45
Ile Lys Ile Trp Thr Gln Asn Arg Arg Met Lys Trp Lys Lys Glu
                50                  55                  60
Glu (2) INFORMATION FOR SEQ ID NO:31:

(i) SEQUENCE CHARACTERISTICS:
(A) LENGTH: 30
(B) TYPE: amino acid
(C) STRANDEDNESS:
(D) TOPOLOGY: linear (ii) MOLECULE TYPE:
(A) DESCRIPTION: protein (iii) HYPOTHETICAL: No (iv) ANTI-SENSE: No (vi) ORIGINAL SOURCE:

(xi) SEQUENCE DESCRIPTION: SEQ ID NO: 31:

Thr Lys Asp Lys Tyr Val Val Asp His Arg His Tyr Ser Arg Thr
                 5                  10                  15
Ile Arg Lys Ala Ala Thr Gly Ser Gln Val Ala Ala Glu Ile Asn
                20                  25                  30